United States Patent
Phan et al.

(10) Patent No.: US 10,682,243 B2
(45) Date of Patent: Jun. 16, 2020

(54) SPINAL JOINT IMPLANT DELIVERY DEVICE AND SYSTEM

(71) Applicant: PROVIDENCE MEDICAL TECHNOLOGY, INC., Pleasanton, CA (US)

(72) Inventors: Christopher U. Phan, Dublin, CA (US); Shigeru Tanaka, Half Moon Bay, CA (US); Edward Liou, Pleasanton, CA (US); Jeffrey D. Smith, Clayton, CA (US); Scott Schneider, San Jose, CA (US)

(73) Assignee: Providence Medical Technology, Inc., Pleasanton, CA (US)

( * ) Notice: Subject to any disclaimer, the term of this patent is extended or adjusted under 35 U.S.C. 154(b) by 0 days.

(21) Appl. No.: 15/768,209

(22) PCT Filed: Oct. 13, 2016

(86) PCT No.: PCT/US2016/056891
§ 371 (c)(1),
(2) Date: Apr. 13, 2018

(87) PCT Pub. No.: WO2017/066475
PCT Pub. Date: Apr. 20, 2017

(65) Prior Publication Data
US 2018/0303631 A1 Oct. 25, 2018

Related U.S. Application Data

(60) Provisional application No. 62/351,795, filed on Jun. 17, 2016, provisional application No. 62/240,754, filed on Oct. 13, 2015.

(51) Int. Cl.
*A61F 2/46* (2006.01)
*A61B 17/70* (2006.01)
(Continued)

(52) U.S. Cl.
CPC ............ *A61F 2/4611* (2013.01); *A61B 17/70* (2013.01); *A61F 2/4455* (2013.01);
(Continued)

(58) Field of Classification Search
CPC ........ A61F 2/46; A61F 2/4601; A61F 2/4603; A61F 2/4611; A61F 2/4455; A61F 2/447
See application file for complete search history.

(56) References Cited

U.S. PATENT DOCUMENTS 1,934,962 A 11/1933 Barry
2,708,376 A 5/1955 Booth
(Continued)

FOREIGN PATENT DOCUMENTS

DE G9304368.6 U1 5/2003
EP 2272436 A1 1/2011
(Continued)

OTHER PUBLICATIONS

US 7,063,700 B2, 06/2006, Michelson (withdrawn)
(Continued)

*Primary Examiner* — Julianna N Harvey
*Assistant Examiner* — Christina NegrelliRodriguez
(74) *Attorney, Agent, or Firm* — Dorsey & Whitney LLP

(57) ABSTRACT

Provided herein are devices, systems, apparatus and methods for accessing the cervical spine via an anterior approach and implanting a spinal fixation member between two vertebrae of the cervical spine in the disc or intervertebral joint space, such as in an ACDF procedure. The delivery device includes a distal end that can be anchored to the spinal fixation member. Once anchored to the spinal fixation member, the delivery device is operable to both advance and attach the spinal fixation member within a cervical disc joint space.

20 Claims, 28 Drawing Sheets

(51) Int. Cl.
*A61F 2/44* (2006.01)
*A61B 17/88* (2006.01)
*A61B 17/16* (2006.01)
*A61B 17/86* (2006.01)
*A61B 17/17* (2006.01)
*A61B 17/80* (2006.01)
*A61F 2/30* (2006.01)

(52) U.S. Cl.
CPC ........ *A61F 2/4601* (2013.01); *A61B 17/1615* (2013.01); *A61B 17/1631* (2013.01); *A61B 17/1757* (2013.01); *A61B 17/8042* (2013.01); *A61B 17/8625* (2013.01); *A61B 17/8875* (2013.01); *A61B 17/8888* (2013.01); *A61F 2/30749* (2013.01); *A61F 2/442* (2013.01); *A61F 2/447* (2013.01); *A61F 2/4603* (2013.01); *A61F 2002/308* (2013.01); *A61F 2002/30261* (2013.01); *A61F 2002/30517* (2013.01); *A61F 2002/30576* (2013.01); *A61F 2002/30578* (2013.01); *A61F 2002/30593* (2013.01); *A61F 2002/30774* (2013.01); *A61F 2002/30787* (2013.01); *A61F 2002/30904* (2013.01); *A61F 2002/4627* (2013.01); *A61F 2002/4629* (2013.01); *A61F 2002/4677* (2013.01); *A61F 2002/4687* (2013.01)

(56) References Cited

U.S. PATENT DOCUMENTS

| | | |
|---|---|---|
| 2,984,241 A | 5/1961 | Carlson |
| 3,486,505 A | 12/1969 | Morrison |
| 4,479,491 A | 10/1984 | Martin |
| 4,530,355 A | 7/1985 | Griggs |
| 4,772,287 A | 9/1988 | Ray et al. |
| 4,877,020 A | 10/1989 | Vich |
| 4,878,915 A | 11/1989 | Brantigan |
| 5,015,247 A | 5/1991 | Michelson |
| 5,026,373 A | 6/1991 | Ray et al. |
| 5,100,405 A | 3/1992 | McLaren |
| 5,135,528 A | 8/1992 | Winston |
| 5,236,460 A | 8/1993 | Barber |
| 5,484,437 A | 1/1996 | Michelson |
| 5,489,307 A | 2/1996 | Kuslich et al. |
| 5,505,732 A | 4/1996 | Michelson |
| 5,527,312 A | 6/1996 | Ray |
| 5,549,679 A | 8/1996 | Kuslich et al. |
| 5,554,191 A | 9/1996 | Lahille et al. |
| 5,571,191 A | 11/1996 | Fitz |
| 5,593,409 A | 1/1997 | Michelson |
| 5,632,747 A | 5/1997 | Scarborough et al. |
| 5,649,945 A | 7/1997 | Ray et al. |
| 5,653,763 A | 8/1997 | Errico et al. |
| 5,665,122 A | 9/1997 | Kambin |
| 5,674,295 A | 10/1997 | Ray et al. |
| 5,720,748 A | 2/1998 | Kuslich et al. |
| 5,741,253 A | 4/1998 | Michelson |
| 5,772,661 A | 6/1998 | Michelson |
| 5,792,044 A | 8/1998 | Foley et al. |
| 5,797,909 A | 8/1998 | Michelson |
| 5,836,948 A | 11/1998 | Zucherman et al. |
| 5,879,353 A | 3/1999 | Terry |
| 5,885,299 A | 3/1999 | Winslow et al. |
| 5,891,147 A | 4/1999 | Moskovitz |
| 5,895,426 A | 4/1999 | Scarborough et al. |
| 5,899,908 A | 5/1999 | Kuslich et al. |
| 5,928,238 A | 7/1999 | Scarborough et al. |
| 5,953,820 A | 9/1999 | Vasudeva |
| 5,961,522 A | 10/1999 | Mehdizadeh |
| 5,976,146 A | 11/1999 | Ogawa et al. |
| 6,008,433 A | 12/1999 | Stone |
| 6,033,405 A | 3/2000 | Winslow et al. |
| 6,045,580 A | 4/2000 | Scarborough et al. |
| 6,063,088 A | 5/2000 | Winslow |
| RE36,758 E | 6/2000 | Fitz |
| 6,080,155 A | 6/2000 | Michelson |
| 6,090,143 A | 7/2000 | Meriwether et al. |
| 6,096,038 A | 8/2000 | Michelson |
| 6,096,046 A | 8/2000 | Weiss |
| 6,099,531 A | 8/2000 | Bonutti |
| 6,102,950 A | 8/2000 | Vaccaro |
| 6,113,602 A | 9/2000 | Sand |
| 6,149,650 A | 11/2000 | Michelson |
| RE37,005 E | 12/2000 | Michelson et al. |
| 6,159,245 A | 12/2000 | Meriwether et al. |
| 6,176,882 B1 | 1/2001 | Biedermann et al. |
| 6,179,873 B1 | 1/2001 | Zientek |
| 6,190,388 B1 | 2/2001 | Michelson et al. |
| 6,190,414 B1 | 2/2001 | Young et al. |
| 6,193,757 B1 | 2/2001 | Foley et al. |
| 6,210,412 B1 | 4/2001 | Michelson |
| RE37,161 E | 5/2001 | Michelson et al. |
| 6,224,595 B1 | 5/2001 | Michelson |
| 6,224,607 B1 | 5/2001 | Michelson |
| 6,224,630 B1 | 5/2001 | Bao et al. |
| 6,245,108 B1 | 6/2001 | Biscup |
| 6,248,110 B1 | 6/2001 | Reiley et al. |
| D444,878 S | 7/2001 | Walter |
| D445,188 S | 7/2001 | Walter |
| 6,264,656 B1 | 7/2001 | Michelson |
| 6,267,763 B1 | 7/2001 | Castro |
| 6,270,498 B1 | 8/2001 | Michelson |
| 6,283,966 B1 | 9/2001 | Boufbur |
| 6,315,795 B1 | 11/2001 | Scarborough et al. |
| 6,325,827 B1 | 12/2001 | Lin |
| 6,371,984 B1 | 4/2002 | Van Dyke et al. |
| 6,371,988 B1 | 4/2002 | Pafford et al. |
| 6,402,784 B1 | 6/2002 | Wardlaw |
| 6,423,063 B1 | 7/2002 | Bonutti |
| 6,423,083 B2 | 7/2002 | Reiley et al. |
| 6,425,919 B1 | 7/2002 | Lambrecht |
| 6,436,098 B1 | 8/2002 | Michelson |
| 6,436,142 B1 | 8/2002 | Paes et al. |
| 6,443,988 B2 | 9/2002 | Felt et al. |
| 6,451,023 B1 | 9/2002 | Salazar et al. |
| 6,454,807 B1 | 9/2002 | Jackson |
| 6,478,796 B2 | 11/2002 | Zucherman et al. |
| 6,500,206 B1 | 12/2002 | Bryan |
| 6,514,256 B2 | 2/2003 | Zucherman et al. |
| 6,530,955 B2 | 3/2003 | Boyle et al. |
| 6,558,390 B2 | 5/2003 | Cragg |
| 6,565,574 B2 | 5/2003 | Michelson |
| 6,569,186 B1 | 5/2003 | Winters et al. |
| 6,575,919 B1 | 6/2003 | Reiley et al. |
| 6,575,979 B1 | 6/2003 | Cragg |
| 6,579,319 B2 | 6/2003 | Goble et al. |
| 6,582,432 B1 | 6/2003 | Michelson |
| 6,607,530 B1 | 8/2003 | Carl et al. |
| 6,610,091 B1 | 8/2003 | Reiley |
| 6,626,905 B1 | 9/2003 | Schmiel et al. |
| 6,632,235 B2 | 10/2003 | Weikel et al. |
| 6,635,060 B2 | 10/2003 | Hanson et al. |
| 6,641,582 B1 | 11/2003 | Hanson et al. |
| 6,648,893 B2 | 11/2003 | Dudasik |
| 6,652,584 B2 | 11/2003 | Michelson |
| 6,663,647 B2 | 12/2003 | Reiley et al. |
| 6,666,866 B2 | 12/2003 | Martz et al. |
| 6,679,886 B2 | 1/2004 | Weikel et al. |
| 6,682,535 B2 | 1/2004 | Hoogland |
| 6,685,742 B1 | 2/2004 | Jackson |
| 6,709,458 B2 | 3/2004 | Michelso |
| 6,712,853 B2 | 3/2004 | Kuslich |
| 6,719,773 B1 | 4/2004 | Boucher et al. |
| 6,723,095 B2 | 4/2004 | Hammerslag |
| 6,733,534 B2 | 5/2004 | Sherman |
| 6,740,093 B2 | 5/2004 | Hochschuler et al. |
| 6,751,875 B2 | 6/2004 | Jones |
| 6,770,074 B2 | 8/2004 | Michelson |
| 6,793,679 B2 | 9/2004 | Michelson |
| 6,805,715 B2 | 10/2004 | Reuter et al. |
| 6,808,537 B2 | 10/2004 | Michelson |
| 6,823,871 B2 | 11/2004 | Schmieding |

(56) References Cited

U.S. PATENT DOCUMENTS

| | | |
|---|---|---|
| 6,840,941 B2 | 1/2005 | Rogers et al. |
| 6,851,430 B2 | 2/2005 | Tsou |
| 6,875,213 B2 | 4/2005 | Michelson |
| 6,899,719 B2 | 5/2005 | Reiley et al. |
| 6,921,403 B2 | 7/2005 | Cragg et al. |
| 6,923,813 B2 | 8/2005 | Phillips et al. |
| 6,958,077 B2 | 10/2005 | Suddaby |
| 6,962,606 B2 | 11/2005 | Michelson |
| 6,964,686 B2 | 11/2005 | Gordon |
| 6,966,930 B2 | 11/2005 | Arnin et al. |
| 6,972,035 B2 | 12/2005 | Michelson |
| 6,979,333 B2 | 12/2005 | Hammerslag |
| 6,986,772 B2 | 1/2006 | Michelson |
| 7,001,385 B2 | 2/2006 | Bonutti |
| 7,008,453 B1 | 3/2006 | Michelson |
| 7,033,362 B2 | 4/2006 | McGahan et al. |
| 7,033,392 B2 | 4/2006 | Schmiel et al. |
| 7,033,394 B2 | 4/2006 | Michelson |
| 7,066,961 B2 | 6/2006 | Michelson |
| D524,443 S | 7/2006 | Blain |
| 7,083,623 B2 | 8/2006 | Michelson |
| 7,096,972 B2 | 8/2006 | Orozco, Jr. |
| 7,101,398 B2 | 9/2006 | Dooris et al. |
| 7,115,128 B2 | 10/2006 | Michelson |
| 7,118,598 B2 | 10/2006 | Michelson |
| 7,128,760 B2 | 10/2006 | Michelson |
| 7,156,877 B2 | 1/2007 | Lotz et al. |
| 7,166,110 B2 | 1/2007 | Yundt |
| 7,175,023 B2 | 2/2007 | Martin |
| 7,179,263 B2 | 2/2007 | Zdeblick et al. |
| 7,207,991 B2 | 4/2007 | Michelson |
| D541,940 S | 5/2007 | Blain |
| 7,220,280 B2 | 5/2007 | Kast et al. |
| 7,261,739 B2 | 8/2007 | Ralph et al. |
| 7,264,622 B2 | 9/2007 | Michelson |
| 7,273,498 B2 | 9/2007 | Bianchi et al. |
| 7,288,093 B2 | 10/2007 | Michelson |
| 7,291,149 B1 | 11/2007 | Michelson |
| 7,300,440 B2 | 11/2007 | Zdeblick et al. |
| 7,326,211 B2 | 2/2008 | Padget et al. |
| 7,326,214 B2 | 2/2008 | Michelson |
| 7,371,238 B2 | 5/2008 | Soboleski et al. |
| 7,399,303 B2 | 7/2008 | Michelson |
| 7,410,501 B2 | 8/2008 | Michelson |
| 7,431,722 B1 | 10/2008 | Michelson |
| 7,445,636 B2 | 11/2008 | Michelson |
| 7,452,359 B1 | 11/2008 | Michelson |
| 7,452,369 B2 | 11/2008 | Barry |
| 7,465,304 B1 | 12/2008 | Haufe et al. |
| 7,476,226 B2 | 1/2009 | Weikel et al. |
| 7,476,251 B2 | 1/2009 | Zucherman et al. |
| 7,479,160 B2 | 1/2009 | Branch et al. |
| 7,491,205 B1 | 2/2009 | Michelson |
| 7,491,240 B1 | 2/2009 | Carver et al. |
| 7,500,992 B2 | 3/2009 | Li |
| 7,517,358 B2 | 4/2009 | Peterson |
| 7,524,333 B2 | 4/2009 | Lambrecht et al. |
| 7,569,054 B2 | 8/2009 | Michelson |
| 7,569,057 B2 | 8/2009 | Liu et al. |
| 7,580,743 B2 | 8/2009 | Bourlion et al. |
| 7,591,851 B2 | 9/2009 | Winslow et al. |
| 7,601,170 B2 | 10/2009 | Winslow et al. |
| 7,608,077 B2 | 10/2009 | Cragg et al. |
| 7,608,107 B2 | 10/2009 | Michelson |
| 7,615,079 B2 | 11/2009 | Flickinger et al. |
| 7,618,451 B2 | 11/2009 | Berez et al. |
| 7,632,291 B2 | 12/2009 | Stephens et al. |
| 7,641,664 B2 | 1/2010 | Pagano |
| 7,645,232 B2 | 1/2010 | Shluzas |
| 7,648,509 B2 | 1/2010 | Stark |
| 7,648,523 B2 | 1/2010 | Mirkovic et al. |
| 7,655,027 B2 | 2/2010 | Michelson |
| 7,655,043 B2 | 2/2010 | Peterman et al. |
| 7,662,173 B2 | 2/2010 | Cragg et al. |
| D611,147 S | 3/2010 | Hanson et al. |
| 7,682,378 B2 | 3/2010 | Truckai et al. |
| 7,686,805 B2 | 3/2010 | Michelson |
| 7,686,807 B2 | 3/2010 | Padget et al. |
| 7,699,878 B2 | 4/2010 | Pavlov et al. |
| D615,653 S | 5/2010 | Horton |
| 7,708,761 B2 | 5/2010 | Petersen |
| 7,722,619 B2 | 5/2010 | Michelson |
| D619,719 S | 7/2010 | Pannu |
| 7,763,024 B2 | 7/2010 | Bertagnoli et al. |
| 7,763,050 B2 | 7/2010 | Winslow et al. |
| 7,776,090 B2 | 8/2010 | Winslow et al. |
| D623,748 S | 9/2010 | Horton et al. |
| D623,749 S | 9/2010 | Horton et al. |
| 7,789,898 B2 | 9/2010 | Peterman |
| D627,468 S | 11/2010 | Richter et al. |
| 7,824,431 B2 | 11/2010 | McCormack |
| 7,837,713 B2 | 11/2010 | Peterson |
| 7,846,183 B2 | 12/2010 | Blain |
| 7,846,184 B2 | 12/2010 | Sasso et al. |
| 7,850,733 B2 | 12/2010 | Baynham et al. |
| 7,862,589 B2 | 1/2011 | Thramann |
| 7,867,277 B1 | 1/2011 | Tohmeh |
| D631,967 S | 2/2011 | Horton |
| 7,879,098 B1 | 2/2011 | Simmons, Jr. |
| 7,887,565 B2 | 2/2011 | Michelson |
| 7,892,261 B2 | 2/2011 | Bonutti |
| 7,892,286 B2 | 2/2011 | Michelson |
| 7,896,803 B2 | 3/2011 | Schara et al. |
| 7,896,903 B2 | 3/2011 | Link |
| 7,901,439 B2 | 3/2011 | Horton |
| 7,914,530 B2 | 3/2011 | Michelson |
| 7,918,891 B1 | 4/2011 | Curran et al. |
| 7,922,729 B2 | 4/2011 | Michelson |
| 7,922,766 B2 | 4/2011 | Grob et al. |
| 7,935,136 B2 | 5/2011 | Alamin et al. |
| 7,938,857 B2 | 5/2011 | Krueger et al. |
| 7,942,903 B2 | 5/2011 | Moskowitz et al. |
| 7,988,712 B2 | 8/2011 | Hale et al. |
| 7,988,714 B2 | 8/2011 | Puekert et al. |
| 7,998,174 B2 | 8/2011 | Malandain et al. |
| 8,007,534 B2 | 8/2011 | Michelson |
| 8,029,540 B2 | 10/2011 | Winslow et al. |
| 8,043,334 B2 | 10/2011 | Fisher et al. |
| 8,052,728 B2 | 11/2011 | Hestad |
| 8,062,303 B2 | 11/2011 | Berry et al. |
| 8,066,705 B2 | 11/2011 | Michelson |
| D650,481 S | 12/2011 | Gottlieb et al. |
| 8,097,034 B2 | 1/2012 | Michelson |
| 8,100,944 B2 | 1/2012 | Lauryssen et al. |
| D653,757 S | 2/2012 | Binder |
| 8,114,158 B2 | 2/2012 | Carl et al. |
| 8,118,838 B2 | 2/2012 | Winslow et al. |
| 8,128,660 B2 | 3/2012 | Mitchel et al. |
| 8,133,261 B2 | 3/2012 | Fisher et al. |
| 8,142,503 B2 | 3/2012 | Malone |
| 8,147,553 B2 | 4/2012 | Vresilovic et al. |
| 8,162,981 B2 | 4/2012 | Vestgaarden |
| 8,172,877 B2 | 5/2012 | Winslow et al. |
| 8,177,872 B2 | 5/2012 | Nelson et al. |
| 8,197,513 B2 | 6/2012 | Fisher et al. |
| 8,206,418 B2 | 6/2012 | Triplett et al. |
| 8,267,966 B2 | 9/2012 | McCormack et al. |
| D674,900 S | 1/2013 | Janice et al. |
| 8,348,979 B2 | 1/2013 | McCormack |
| 8,361,152 B2 | 1/2013 | McCormack et al. |
| 8,366,748 B2 | 2/2013 | Kleiner |
| D677,791 S | 3/2013 | Danacioglu et al. |
| 8,394,107 B2 | 3/2013 | Fanger et al. |
| 8,394,129 B2 | 3/2013 | Morgenstern et al. |
| D681,205 S | 4/2013 | Farris et al. |
| 8,425,558 B2 | 4/2013 | McCormack et al. |
| 8,512,347 B2 | 8/2013 | McCormack et al. |
| 8,523,908 B2 | 9/2013 | Malone |
| 8,529,609 B2 | 9/2013 | Helgerson et al. |
| 8,623,054 B2 | 1/2014 | McCormack et al. |
| 8,668,722 B2 | 3/2014 | Pavlov et al. |
| 8,753,345 B2 | 6/2014 | Mccormack et al. |
| 8,753,347 B2 | 6/2014 | McCormack et al. |
| 8,764,755 B2 | 7/2014 | Michelson |

(56) References Cited

U.S. PATENT DOCUMENTS

| | | |
|---|---|---|
| 8,828,062 B2 | 9/2014 | McCormack et al. |
| 8,834,530 B2 | 9/2014 | McCormack |
| 8,845,727 B2 | 9/2014 | Gottlieb et al. |
| 8,870,882 B2 | 10/2014 | Kleiner |
| D723,690 S | 3/2015 | McCormack et al. |
| D723,691 S | 3/2015 | McCormack et al. |
| 8,998,905 B2 | 4/2015 | Marik et al. |
| 9,005,288 B2 | 4/2015 | Mccormack et al. |
| 9,011,492 B2 | 4/2015 | McCormack et al. |
| D732,667 S | 6/2015 | McCormack et al. |
| 9,186,193 B2 | 11/2015 | Kleiner et al. |
| D745,156 S | 12/2015 | McCormack et al. |
| 9,211,198 B2 | 12/2015 | Michelson |
| 9,220,608 B2 | 12/2015 | McKay |
| D750,249 S | 2/2016 | Grimberg, Jr. et al. |
| 9,271,765 B2 | 3/2016 | Blain |
| 9,333,086 B2 | 5/2016 | McCormack et al. |
| 9,358,127 B2 | 6/2016 | Duffield et al. |
| 9,381,049 B2 | 7/2016 | McCormack et al. |
| 9,427,264 B2 | 8/2016 | Kleiner et al. |
| 9,504,583 B2 | 11/2016 | Blain |
| 9,622,791 B2 | 4/2017 | Mccormack et al. |
| 9,622,873 B2 | 4/2017 | Mccormack |
| 9,622,874 B2 | 4/2017 | Mccormack et al. |
| 9,629,665 B2 | 4/2017 | Mccormack et al. |
| 9,717,403 B2 | 8/2017 | Kleiner et al. |
| 10,039,649 B2 | 8/2018 | Mccormack et al. |
| 10,111,670 B2 | 10/2018 | Lorenzo et al. |
| 10,149,673 B2 | 12/2018 | Mccormack et al. |
| 10,172,721 B2 | 1/2019 | Mccormack et al. |
| D841,165 S | 2/2019 | Mccormack et al. |
| 10,201,375 B2 | 2/2019 | Mccormack et al. |
| 10,219,910 B2 | 3/2019 | Mccormack |
| 10,226,285 B2 | 3/2019 | Mccormack et al. |
| 10,238,501 B2 | 3/2019 | Mccormack et al. |
| 10,456,175 B2 | 10/2019 | McCormack et al. |
| 2001/0004710 A1 | 6/2001 | Felt et al. |
| 2001/0047208 A1 | 11/2001 | Michelson |
| 2002/0026195 A1 | 2/2002 | Layne et al. |
| 2002/0068941 A1 | 6/2002 | Hanson et al. |
| 2002/0107519 A1 | 8/2002 | Dixon et al. |
| 2002/0143343 A1 | 10/2002 | Castro |
| 2002/0147496 A1 | 10/2002 | Belef et al. |
| 2002/0147497 A1 | 10/2002 | Belef et al. |
| 2002/0165612 A1 | 11/2002 | Gerber et al. |
| 2002/0169471 A1 | 11/2002 | Ferdinand |
| 2003/0023312 A1 | 1/2003 | Thalgott |
| 2003/0028251 A1 | 2/2003 | Mathews |
| 2003/0032962 A1 | 2/2003 | McGahan et al. |
| 2003/0033017 A1 | 2/2003 | Lotz et al. |
| 2003/0105526 A1 | 6/2003 | Bryant et al. |
| 2003/0109928 A1 | 6/2003 | Pasquet et al. |
| 2003/0139816 A1 | 7/2003 | Michelson |
| 2003/0144737 A1 | 7/2003 | Sherman |
| 2003/0158553 A1 | 8/2003 | Michelson |
| 2003/0225416 A1 | 12/2003 | Bonvallet et al. |
| 2004/0059337 A1 | 3/2004 | Hanson et al. |
| 2004/0073217 A1 | 4/2004 | Michelson |
| 2004/0087948 A1 | 5/2004 | Suddaby |
| 2004/0087956 A1 | 5/2004 | Weikel et al. |
| 2004/0106999 A1 | 6/2004 | Mathews |
| 2004/0133277 A1 | 7/2004 | Michelson |
| 2004/0133280 A1 | 7/2004 | Trieu |
| 2004/0162562 A1 | 8/2004 | Martz |
| 2004/0215344 A1 | 10/2004 | Hochshculer et al. |
| 2005/0010294 A1 | 1/2005 | Michelson |
| 2005/0015149 A1 | 1/2005 | Michelson |
| 2005/0027358 A1 | 2/2005 | Suddaby |
| 2005/0033432 A1 | 2/2005 | Gordon et al. |
| 2005/0049705 A1 | 3/2005 | Hale et al. |
| 2005/0055096 A1 | 3/2005 | Serhan et al. |
| 2005/0065518 A1 | 3/2005 | Michelson |
| 2005/0065519 A1 | 3/2005 | Michelson |
| 2005/0065608 A1 | 3/2005 | Michelson |
| 2005/0065609 A1 | 3/2005 | Wardlaw |
| 2005/0080422 A1 | 4/2005 | Otte et al. |
| 2005/0090829 A1 | 4/2005 | Martz et al. |
| 2005/0090901 A1 | 4/2005 | Studer |
| 2005/0119680 A1 | 6/2005 | Dykes |
| 2005/0124993 A1 | 6/2005 | Chappuis |
| 2005/0149192 A1 | 7/2005 | Zucherman et al. |
| 2005/0159650 A1 | 7/2005 | Raymond et al. |
| 2005/0159746 A1 | 7/2005 | Grob et al. |
| 2005/0177240 A1 | 8/2005 | Blain |
| 2005/0182417 A1 | 8/2005 | Pagano |
| 2005/0216018 A1 | 9/2005 | Sennett |
| 2005/0234455 A1* | 10/2005 | Binder ............... A61B 17/8047 606/294 |
| 2005/0240188 A1 | 10/2005 | Chow et al. |
| 2005/0251146 A1 | 11/2005 | Martz et al. |
| 2005/0251257 A1 | 11/2005 | Mitchell et al. |
| 2005/0267480 A1 | 12/2005 | Suddaby |
| 2006/0004367 A1 | 1/2006 | Alamin et al. |
| 2006/0015184 A1 | 1/2006 | Winterbottom et al. |
| 2006/0036243 A1 | 2/2006 | Sasso et al. |
| 2006/0036247 A1 | 2/2006 | Michelson |
| 2006/0036323 A1 | 2/2006 | Carl et al. |
| 2006/0041311 A1 | 2/2006 | McLeer |
| 2006/0058793 A1 | 3/2006 | Michelson |
| 2006/0058878 A1 | 3/2006 | Michelson |
| 2006/0069442 A1 | 3/2006 | Michelson |
| 2006/0079905 A1 | 4/2006 | Beyar et al. |
| 2006/0079962 A1 | 4/2006 | Michelson |
| 2006/0085068 A1 | 4/2006 | Barry |
| 2006/0085074 A1 | 4/2006 | Raiszadeh |
| 2006/0095028 A1 | 5/2006 | Bleich |
| 2006/0095036 A1 | 5/2006 | Hammerslag |
| 2006/0111779 A1 | 5/2006 | Peterson |
| 2006/0111780 A1 | 5/2006 | Petersen |
| 2006/0111781 A1 | 5/2006 | Petersen |
| 2006/0142762 A1 | 6/2006 | Michelson |
| 2006/0149289 A1 | 7/2006 | Winslow et al. |
| 2006/0184172 A1 | 8/2006 | Michelson |
| 2006/0189991 A1 | 8/2006 | Bickley |
| 2006/0190081 A1 | 8/2006 | Kraus et al. |
| 2006/0195109 A1 | 8/2006 | McGahan et al. |
| 2006/0200137 A1 | 9/2006 | Soboleski et al. |
| 2006/0200138 A1 | 9/2006 | Michelson |
| 2006/0200139 A1 | 9/2006 | Michelson |
| 2006/0206118 A1 | 9/2006 | Kim et al. |
| 2006/0217812 A1 | 9/2006 | Lambrecht et al. |
| 2006/0235391 A1 | 10/2006 | Sutterlin, III |
| 2006/0241597 A1 | 10/2006 | Mitchell et al. |
| 2006/0241626 A1 | 10/2006 | McGahan et al. |
| 2006/0241758 A1 | 10/2006 | Peterman et al. |
| 2006/0247632 A1 | 11/2006 | Winslow et al. |
| 2006/0247633 A1 | 11/2006 | Winslow et al. |
| 2006/0247650 A1 | 11/2006 | Yerby et al. |
| 2006/0259142 A1 | 11/2006 | Dooris et al. |
| 2006/0271195 A1 | 11/2006 | Thramann |
| 2006/0276790 A1 | 12/2006 | Dawson et al. |
| 2006/0276801 A1 | 12/2006 | Yerby et al. |
| 2006/0276897 A1 | 12/2006 | Winslow et al. |
| 2006/0293663 A1 | 12/2006 | Walkenhorst et al. |
| 2007/0016195 A1 | 1/2007 | Winslow et al. |
| 2007/0016196 A1 | 1/2007 | Winslow et al. |
| 2007/0016218 A1 | 1/2007 | Winslow et al. |
| 2007/0032871 A1 | 2/2007 | Michelson |
| 2007/0043362 A1 | 2/2007 | Malandain et al. |
| 2007/0050031 A1 | 3/2007 | Khosrowshahi |
| 2007/0055245 A1 | 3/2007 | Sasso et al. |
| 2007/0055263 A1 | 3/2007 | Way et al. |
| 2007/0073402 A1 | 3/2007 | Vresilovic et al. |
| 2007/0083265 A1 | 4/2007 | Malone |
| 2007/0123863 A1 | 5/2007 | Winslow et al. |
| 2007/0123888 A1 | 5/2007 | Bleich et al. |
| 2007/0135814 A1 | 6/2007 | Farris |
| 2007/0135921 A1 | 6/2007 | Park |
| 2007/0149976 A1 | 6/2007 | Hale et al. |
| 2007/0149983 A1 | 6/2007 | Link |
| 2007/0150061 A1 | 6/2007 | Trieu |
| 2007/0161991 A1 | 7/2007 | Altarac et al. |
| 2007/0179617 A1 | 8/2007 | Brown et al. |
| 2007/0179619 A1 | 8/2007 | Grob et al. |

(56) References Cited

U.S. PATENT DOCUMENTS

| | | |
|---|---|---|
| 2007/0225721 A1 | 9/2007 | Thelen et al. |
| 2007/0225812 A1 | 9/2007 | Gill |
| 2007/0244483 A9 | 10/2007 | Winslow et al. |
| 2007/0250167 A1* | 10/2007 | Bray ............... A61F 2/4455 623/17.11 |
| 2007/0276491 A1 | 11/2007 | Ahrens |
| 2007/0282441 A1 | 12/2007 | Stream et al. |
| 2007/0288014 A1 | 12/2007 | Shadduck et al. |
| 2007/0299451 A1 | 12/2007 | Tulkis |
| 2008/0015581 A1 | 1/2008 | Eckman |
| 2008/0021457 A1 | 1/2008 | Anderson et al. |
| 2008/0021464 A1 | 1/2008 | Morin et al. |
| 2008/0058954 A1 | 3/2008 | Trieu |
| 2008/0065219 A1 | 3/2008 | Dye |
| 2008/0097436 A1 | 4/2008 | Culbert et al. |
| 2008/0108996 A1 | 5/2008 | Padget et al. |
| 2008/0140207 A1 | 6/2008 | Olmos et al. |
| 2008/0154377 A1 | 6/2008 | Voellmicke |
| 2008/0161810 A1 | 7/2008 | Melkent |
| 2008/0161929 A1 | 7/2008 | McCormack et al. |
| 2008/0167657 A1 | 7/2008 | Greenhaigh |
| 2008/0177311 A1 | 7/2008 | Winslow et al. |
| 2008/0216846 A1 | 9/2008 | Levin |
| 2008/0234677 A1 | 9/2008 | Dahners et al. |
| 2008/0234758 A1 | 9/2008 | Fisher et al. |
| 2008/0249571 A1 | 10/2008 | Sasso et al. |
| 2008/0255564 A1 | 10/2008 | Michelson |
| 2008/0255618 A1 | 10/2008 | Fisher et al. |
| 2008/0255622 A1 | 10/2008 | Mickiewicz et al. |
| 2008/0255666 A1 | 10/2008 | Fisher et al. |
| 2008/0255667 A1 | 10/2008 | Horton |
| 2008/0287955 A1 | 11/2008 | Michelson |
| 2008/0306537 A1 | 12/2008 | Culbert |
| 2008/0312744 A1 | 12/2008 | Vresilovic et al. |
| 2009/0131986 A1 | 5/2009 | Lee et al. |
| 2009/0138053 A1 | 5/2009 | Assell et al. |
| 2009/0177215 A1 | 7/2009 | Stack et al. |
| 2009/0177237 A1 | 7/2009 | Zucherman et al. |
| 2009/0234397 A1 | 9/2009 | Petersen |
| 2009/0248076 A1 | 10/2009 | Reynolds et al. |
| 2009/0263461 A1 | 10/2009 | McKay |
| 2009/0270929 A1 | 10/2009 | Suddaby et al. |
| 2009/0275994 A1 | 11/2009 | Phan et al. |
| 2010/0086185 A1 | 4/2010 | Weiss |
| 2010/0093829 A1 | 4/2010 | Gorman |
| 2010/0111829 A1 | 5/2010 | Drapeau et al. |
| 2010/0114318 A1 | 5/2010 | Gittings et al. |
| 2010/0145391 A1 | 6/2010 | Kleiner |
| 2010/0145459 A1 | 6/2010 | Mcdonough et al. |
| 2010/0211104 A1 | 8/2010 | Moumene et al. |
| 2011/0004247 A1 | 1/2011 | Lechmann et al. |
| 2011/0022089 A1 | 1/2011 | Assell et al. |
| 2011/0054613 A1 | 3/2011 | Hansen |
| 2011/0077686 A1 | 3/2011 | Mishra et al. |
| 2011/0082548 A1 | 4/2011 | Assell et al. |
| 2011/0144755 A1 | 6/2011 | Baynham et al. |
| 2011/0184470 A1 | 7/2011 | Gorek et al. |
| 2011/0190821 A1 | 8/2011 | Chin et al. |
| 2011/0245930 A1 | 10/2011 | Alley et al. |
| 2011/0295327 A1 | 12/2011 | Moskowitz et al. |
| 2011/0307061 A1 | 12/2011 | Assell et al. |
| 2012/0010659 A1 | 1/2012 | Angert et al. |
| 2012/0010662 A1 | 1/2012 | O'Neil et al. |
| 2012/0010669 A1 | 1/2012 | O'Neil et al. |
| 2012/0065613 A1 | 3/2012 | Pepper et al. |
| 2012/0130496 A1 | 5/2012 | Duffield et al. |
| 2012/0143334 A1 | 6/2012 | Boyce et al. |
| 2012/0215259 A1 | 8/2012 | Cannestra |
| 2012/0265250 A1 | 10/2012 | Ali |
| 2012/0283776 A1 | 11/2012 | Mishra |
| 2012/0323242 A1 | 12/2012 | Tsuang et al. |
| 2013/0013070 A1 | 1/2013 | McCormack et al. |
| 2013/0023889 A1* | 1/2013 | Blain ............... A61B 17/1728 606/96 |
| 2013/0110168 A1 | 5/2013 | McCormack et al. |
| 2013/0110243 A1 | 5/2013 | Patterson et al. |
| 2013/0123922 A1 | 5/2013 | McCormack et al. |
| 2013/0144389 A1 | 6/2013 | Bonutti |
| 2013/0226239 A1 | 8/2013 | Altarac et al. |
| 2013/0253649 A1 | 9/2013 | Davis |
| 2013/0274763 A1 | 10/2013 | Drapeau et al. |
| 2013/0310839 A1 | 11/2013 | McCormack et al. |
| 2013/0310943 A1 | 11/2013 | McCormack et al. |
| 2013/0317548 A1 | 11/2013 | Malone |
| 2013/0338720 A1 | 12/2013 | Kleiner |
| 2014/0012318 A1 | 1/2014 | Goel |
| 2014/0275801 A1 | 9/2014 | Menchaca et al. |
| 2014/0296916 A1 | 10/2014 | Mccormack et al. |
| 2015/0100129 A1 | 4/2015 | Waugh et al. |
| 2015/0201977 A1 | 7/2015 | Mccormack et al. |
| 2015/0342648 A1 | 12/2015 | Mccormack et al. |
| 2015/0342649 A1 | 12/2015 | Mccormack et al. |
| 2016/0008040 A1 | 1/2016 | Mccormack et al. |
| 2016/0242754 A1 | 8/2016 | Mccormack et al. |
| 2016/0250035 A1 | 9/2016 | De Villiers et al. |
| 2017/0027713 A1 | 2/2017 | Kleiner |
| 2017/0189199 A1 | 7/2017 | Maier et al. |
| 2017/0348027 A1 | 12/2017 | Mccormack et al. |
| 2017/0354444 A1 | 12/2017 | Mccormack et al. |
| 2018/0161077 A1 | 6/2018 | Mccormack et al. |
| 2018/0303631 A1 | 10/2018 | Phan et al. |
| 2019/0209151 A1 | 7/2019 | Mccormack et al. |
| 2019/0209227 A1 | 7/2019 | Tanaka et al. |
| 2019/0239932 A1 | 8/2019 | Mccormack et al. |
| 2019/0240041 A1 | 8/2019 | Mccormack et al. |
| 2019/0247099 A1 | 8/2019 | McCormack et al. |
| 2019/0247614 A1 | 8/2019 | Hart et al. |
| 2019/0307571 A1 | 10/2019 | Mccormack |
| 2019/0307572 A1 | 10/2019 | Mccormack et al. |
| 2019/0350626 A1 | 11/2019 | Mccormack et al. |

FOREIGN PATENT DOCUMENTS

| | | |
|---|---|---|
| FR | 2722980 A1 | 2/1996 |
| WO | 9829026 A2 | 7/1998 |
| WO | 99/49818 A1 | 10/1999 |
| WO | 00/35388 A1 | 6/2000 |
| WO | 00/53126 A1 | 9/2000 |
| WO | 01/01895 A1 | 1/2001 |
| WO | 02/34120 A2 | 5/2002 |
| WO | 2002/038062 | 5/2002 |
| WO | 02/076335 A2 | 10/2002 |
| WO | 02076335 | 10/2002 |
| WO | 2006058221 | 6/2006 |
| WO | 2006130791 | 12/2006 |
| WO | 2007120903 A2 | 10/2007 |
| WO | 2008083349 A1 | 7/2008 |
| WO | 2008127978 A2 | 10/2008 |
| WO | 2008153732 A1 | 12/2008 |
| WO | 2009089367 | 7/2009 |
| WO | 2009148619 | 12/2009 |
| WO | 2010030994 | 3/2010 |
| WO | 2010074714 | 7/2010 |
| WO | 2010107692 A1 | 9/2010 |
| WO | 2011050140 A1 | 4/2011 |
| WO | 2013043584 A2 | 3/2013 |
| WO | 2014188280 A2 | 11/2014 |
| WO | 2016049784 | 4/2016 |

OTHER PUBLICATIONS

Atul Goel, Facetal distraction as treatment for single- and multilevel cervical spondylotic radiculopathy and myelopathy: a preliminary report, J Neurosurg Spine, Jun. 2011, pp. 689-696.

Press Release, Interventional Spine, Inc., Interventional Spine, Inc. Introduces the PERPOS Fusion Facet Prep Kit, Oct. 14, 2008, 1 Page.

Press Release, minSURG Corp., Orthopedic Development Corporation's TruFUSE Procedure Tops 1,750 Patients in First Year, Sep. 24, 2007, 1 Page.

Extended European Search Report dated Jun. 26, 2019 in connection with European Patent Application No. 16856210.6, 9 pages.

(56) References Cited

OTHER PUBLICATIONS

Press Release, Interventional Spine, Inc., FDA Grants Conditional Approval to Interventional Spine's PercuDyn System IDE Application, Jul. 1, 2008, 1 Page.
Stein, et al., "Percutaneous Facet Joint Fusion: Preliminary Experience," Journal of Vascular and Interventional Radiology, Jan.-Feb. 1993, pp. 69-74, vol. 4, No. 1.

\* cited by examiner

SPINAL JOINT IMPLANT DELIVERY DEVICE AND SYSTEM

CROSS REFERENCE TO RELATED APPLICATIONS

This application claims priority to U.S. Patent Application No. 62/240,754, filed Oct. 13, 2015 and entitled Spinal Joint Implant Delivery Device and to U.S. Patent Application No. 62/351,795, filed Jun. 17, 2016 and entitled Spinal Joint Implant Delivery Device, each of which is hereby incorporated by reference.

FIELD

This invention relates generally to medical devices and methods, and more specifically to devices and methods related to use of a spinal joint implant delivery device.

BACKGROUND

Chronic neck and back problems cause pain and disability for a large segment of today's population. Adverse spinal conditions may be characteristic of age. In particular, spinal stenosis and facet arthropathy may increase with age. Spinal stenosis results in a reduction of foraminal area, which may compress cervical nerve roots and cause radicular pain. Both neck extension and ipsilateral rotation, in contrast to neck flexion, may further reduce the foraminal area and contribute to pain, nerve root compression, and other neural injury.

Cervical disc herniations may be a factor in spinal stenosis and may predominantly present upper extremity radicular symptoms. In this case, treatment may take the form of closed traction. A number of closed traction devices are available that alleviate pain by pulling on the head to increase foraminal height. Cervical disc herniations may also be treated with anterior or posterior surgery to remove the herniated disc and replace it with an implant, bone graft, or combination of the same to support, fixate and promote cervical fusion.

It would be advantageous to have improved devices, systems, and methods for performing cervical spinal fusion procedures via anterior access approaches. Ideally, such devices, systems, and methods would allow for minimally invasive or less invasive access and fixation, as well as helping ensure proper placement of the fixation devices. At least some of these objects will be met by the embodiments described herein.

BRIEF SUMMARY

The various embodiments described herein provide devices, systems, and methods for accessing the cervical spine via an anterior approach and implanting a spinal fixation member between two vertebrae of the cervical spine in the disc or intervertebral joint space. The embodiments described below generally include a delivery device, through which or along which one or more spinal fixation devices and tools may be advanced. The delivery devices described herein generally include a distal end that can be anchored to the spinal fixation member. Once anchored to the spinal fixation member, the delivery device is operable to both advance and attach the spinal fixation member within a cervical disc joint space.

In one aspect, a delivery device for guiding a fixation member to a spine is provided. The delivery device may include an anchor shaft having a distal portion and a proximal portion extending from the distal portion, the distal portion being keyed or threaded to anchor onto the fixation member and a guide member operably associated with the anchor shaft.

In some embodiments, the guide member is slidably coupled with anchor shaft. The guide member may be a double or single cannulated member slidably coupled with the anchor shaft. In some aspects, the anchor shaft is a cannulated tube or solid rod. The delivery device may further comprise a screw guide operably connected to the anchor shaft. The screw guide may be formed monolithically or integrally with the guide member. The screw guide may include one or more integrally formed or removable angled lumen to set a trajectory for a bone screw. In some aspects, the guide member is a guidewire extending adjacent the anchor shaft and configured to anchor onto the fixation member. The guide member may define at least one drill/drive path therein.

In another aspect, a system for guiding and securing a fixation member to a spine is provided. The system may include an intervertebral implant delivery device including: an anchor shaft having a distal portion and a proximal portion extending from the distal portion, the distal portion being releasably affixed to anchor onto the fixation member and a guide member operably connected to the anchor shaft. The system may further include a drill or driver member having a first end and slidably coupled with the guide member adjacent the anchor shaft.

In some embodiments, the guide member is a single or double cannulated member slidably coupled with the anchor shaft and the drill or driver member. The drill or driver member may be releasably coupled with the guide member. In some aspects, the anchor shaft is a cannulated tube and the system further includes a guidewire slidably received within the cannulated anchor shaft. The guidewire is operable to guide and position a cannulated screw onto the fixation member.

In some aspects, the drill or driver member is cannulated to receive a shaft therein to preset an angle of the first end of the drill or driver member for bone screw insertion into the fixation member. The first end of the drill or driver member includes a coupling that permits the drill or driver member to rotate and articulate with a bone screw at a desired angle. The coupling is selected from a group consisting of a universal joint, a coil spring, or a relief cut tube portion.

In another aspect, a method of implanting a spinal fixation implant is provided. The method may include advancing a delivery device into a joint between two adjacent vertebrae. The delivery device includes a fixation member releasably attached to a distal end thereto. The method further includes advancing a drill or driver member adjacent the delivery device, and attaching the fixation member to at least one of the two adjacent vertebrae.

In some embodiments, the method further includes guiding a bone screw releasably attached to the drill or driver member into the fixation member at a desired angle.

In some aspects, an apparatus for guiding a fixation member to a cervical disc joint space in a spine in a surgical procedure, such as an ACDF procedure is disclosed. The apparatus includes a delivery device. The delivery device includes an anchor shaft comprising a central lumen defining a longitudinal axis, a distal portion and a proximal portion extending from the distal portion; and a guide member operably associated with the anchor shaft, the guide member defining a first lumen coaxial with the central lumen, two angled lumen offset from the first lumen and at least one fixation member engagement feature. The apparatus further includes a fixation member having at least one threaded opening and at least one guide member engagement feature such that when the guide member engagement feature receives the fixation member engagement feature, the engagement hinders rotation of the fixation member relative to the guide member.

In some aspects, the apparatus, and more specifically the delivery device, further includes a rod member having at least one threaded end extending at least partially through the central lumen of the anchor shaft to releasably engage the threaded opening of the fixation member.

In some aspects, the apparatus, and more specifically the delivery device, further includes a handle, the handle operably coupled to the proximal portion of the anchor shaft and rotatably coupled to the rod, wherein rotation of the rod releasably engages the rod with the fixation member.

In various aspects, the at least one fixation member engagement feature includes at least one, and preferably two slots. In some aspects, the first angled lumen defines a first trajectory that is angled relative to the longitudinal axis and the second angled lumen defines a second trajectory that is angled relative to the longitudinal axis. The first trajectory may be different from the second trajectory.

In an aspect, the fixation member further comprises two angled threaded apertures offset from the at least one threaded opening, the two angled threaded apertures coextensive or coaxial with a respective angled lumen of the guide member when the guide member and the fixation member are engaged.

In some aspects, when the guide member and the fixation member are engaged, the opening of the fixation member is coextensive or coaxial with the central lumen of the anchor shaft. In various aspects, a surface of the guide member and a surface of the fixation member abut each other. In various aspects, the guide member is slidably coupled with anchor shaft.

In one aspect, a system for guiding and securing a fixation member to a cervical disc joint space in a spine in a surgical procedure, such as an ACDF procedure is disclosed. The system includes a fixation member delivery device. The delivery device includes an anchor shaft comprising a central lumen defining a longitudinal axis, a distal portion and a proximal portion extending from the distal portion; and a guide member operably associated with the anchor shaft, the guide member defining a first lumen coaxial with the central lumen, two angled lumen offset from the first lumen and at least one fixation member engagement feature. In some aspects, the system further includes a fixation member having at least one threaded opening and at least one guide member engagement feature such that when the guide member engagement feature receives the fixation member engagement feature, the engagement hinders rotation of the fixation member relative to the guide member. In some aspects, the system may also include a drive member having a first end operably associated with the guide member adjacent the anchor shaft.

In some aspects of the system, the delivery device further comprises a rod member having at least one threaded end extending at least partially through the central lumen of the anchor shaft to releasably engage the threaded opening of the fixation member.

In some aspects of the system, the device further comprises a handle, the handle operably coupled to the proximal portion of the anchor shaft and rotatably coupled to the rod, wherein rotation of the rod releasably engages the rod with the fixation member.

In some aspects of the system, the fixation member further comprises two angled threaded apertures offset from the at least one threaded opening, the two angled threaded apertures coextensive or coaxial with a respective angled lumen of the guide member when the guide member and the fixation member are engaged. The first trajectory may guide a first fastener to a superior vertebral surface and the second trajectory guides a second fastener to an inferior vertebral surface.

In some aspects, the system further comprises at least one fastener, the at least one fastener received in one of the two angled threaded apertures of the fixation member to secure the fixation member to a vertebral surface. In some aspects, the fastener is an anti-backout screw or a self-locking screw, with an interference thread at the head of the screw.

In some aspects, the first end of the drive member includes a coupling that permits the drive member to rotate and/or articulate with a fastener at a desired angle to deploy the fastener at a desired angle with minimal tissue retraction.

In some aspects, the coupling is selected from a group consisting of a universal joint, a coil spring, or a relief cut tube portion.

A method of implanting a spinal fixation implant is disclosed. In some aspects, the method includes advancing a delivery apparatus into a disc joint space between two adjacent vertebrae in an ACDF procedure. The delivery apparatus includes an anchor shaft comprising a central lumen defining a longitudinal axis, a distal portion and a proximal portion extending from the distal portion; a guide member operably associated with the anchor shaft, the guide member defining a first lumen coaxial with the central lumen, two angled lumen offset from the first lumen and at least one fixation member engagement feature; and a fixation member having at least one threaded opening and at least one guide member engagement feature such that when the guide member engagement feature receives the fixation member engagement feature, the engagement hinders rotation of the fixation member relative to the guide member.

In some aspects, the method further includes advancing a drill/drive member adjacent the delivery apparatus, the drill/drive member having a fastener releasably attached to a first end of the drill/drive member. In some aspects, advancing the fastener through the one of the two angled lumen of the guide member to attach the fixation member to at least one of the two adjacent vertebrae. In some aspects, the first end of the drill/drive member includes a coupling that permits the drill/drive member to rotate and/or articulate with a fastener at a desired angle to deploy the fastener at a desired angle with minimal tissue retraction. In some aspects, the coupling is selected from a group consisting of a universal joint, a coil spring, or a relief cut tube portion. In some aspects, the fastener is an anti-backout screw or a self-locking screw, with an interference thread at the head of the screw.

Additional embodiments and features are set forth in part in the description that follows, and will become apparent to those skilled in the art upon examination of the specification or may be learned by the practice of the disclosed subject matter. A further understanding of the nature and advantages of the present disclosure may be realized by reference to the remaining portions of the specification and drawings, which form part of the disclosure. One of skill in the art will understand that each of the various aspects and features of the disclosure may advantageously be used separately in some instances, or in combination with other aspects and features of the disclosure in other instances.

BRIEF DESCRIPTION OF THE DRAWINGS

The accompanying drawings, which are incorporated into and constitute a part of the specification, illustrate embodiments of the disclosure and, together with the general description above and the detailed description below, serve to explain the principles of these embodiments.

DETAILED DESCRIPTION

A herniated or degenerative disc may cause pain, tingling, numbness and/or weakness. Such a disc may be removed through an incision in the front of the spine through the throat area (also known as an anterior approach) to relieve spinal cord or nerve root pressure. After the disc is removed, a bone graft is inserted to fuse together the bones above and below the disc space. This procedure is generally known as Anterior Cervical Discectomy and Fusion (ACDF).

The various embodiments described herein provide devices, systems, and methods for accessing the cervical spine via an anterior approach and implanting a spinal fixation member (e.g., a cage, spacer, graft, implant or etc.) between two adjacent vertebrae after a herniated or degenerated disc is removed. The devices, systems and apparatus may be single use and/or disposable or include single use and/or disposable components. The embodiments allow for an anterior approach using minimally invasive or less invasive techniques. The embodiments described below generally include a delivery device, through which or along which one or more fixation devices may be advanced.

According to the present disclosure, a surgeon may advance the delivery device into the disc space from outside the patient though a minimally invasive or less invasive incision, and then may hold the delivery device via a handle or proximal end residing outside the patient. The delivery device can be used to advance drills, awls, plates, rods, and/or screws from a percutaneous approach with or without direct visualization. Some of the devices, systems, and methods described herein may include, be performed using, or be similar to, one or more components of the DTRAX® Spinal System, from Providence Medical Technology, Inc. (www.providencemt.com). Various components of the DTRAX® Spinal System may be modified or adjusted, according to various embodiments, for uses described herein.

Figure 1:
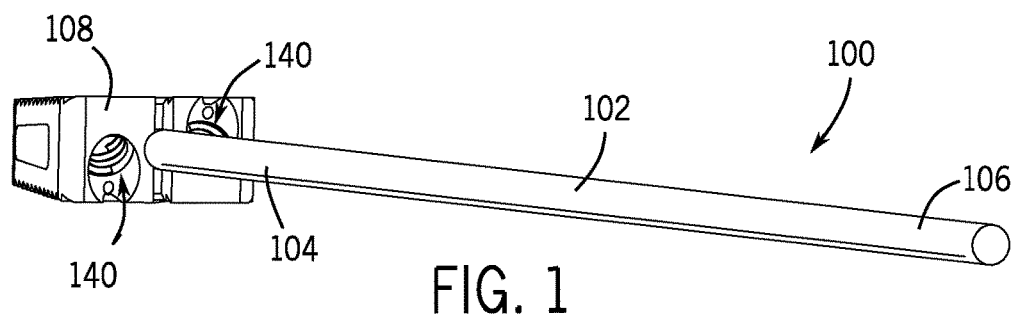
FIG. 1 is a perspective view of a delivery device in accordance with an embodiment of the present disclosure.
Figure 2:
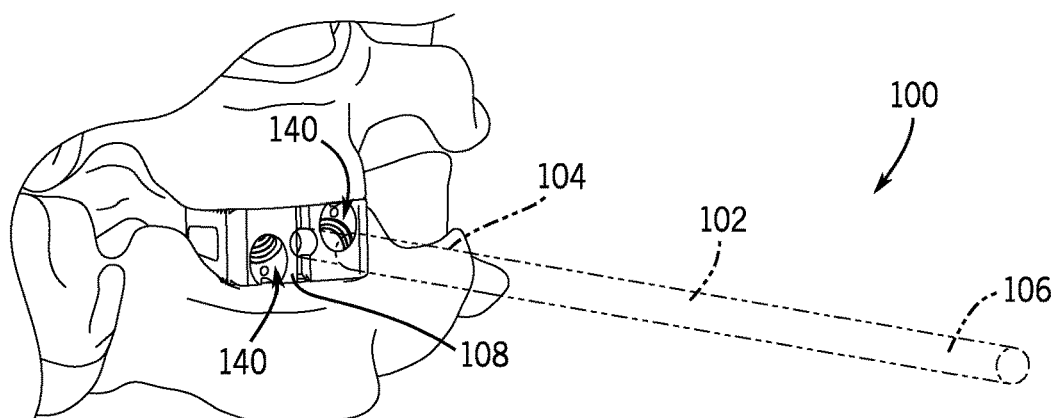
FIG. 2 is a perspective view of the delivery device of FIG. 1 positioned in relation to vertebrae of a cervical spine in accordance with an embodiment of the present disclosure.

Referring to FIGS. 1 and 2, a guide tool or delivery device 100 according to one embodiment of the present disclosure may include an elongated anchor shaft 102 having a distal portion 104 and a proximal portion 106 extending from the distal portion 104. The anchor shaft 102 may be generally long enough to extend from the distal portion 104 to a location outside a patient, where at least a portion of the anchor shaft 102 (e.g., the proximal portion 106) can be held and manipulated by a surgeon. The distal portion 104 and the proximal portion 106 may be two pieces attached together or, in some embodiments, may be formed monolithically or integrally together as a single piece. The anchor shaft 102, which may be a solid rod or solid shaft or a cannulated tube, may be sized and shaped to releasably anchor the anchor shaft 102 to a fixation member 108 (e.g., a CAVUX™ Cervical Cage-L from Providence Medical Technology, Inc.). For example, the distal portion 104 of the anchor shaft 102 may be keyed or may include threading or the like to retain the anchor shaft 102 releasably to the fixation member 108. In some embodiments, the fixation member 108 may be connected symmetrically to the anchor shaft 102 so the delivery device 100 may be positioned irrespective to a position of a patient or the fixation member 108.

Figure 11:
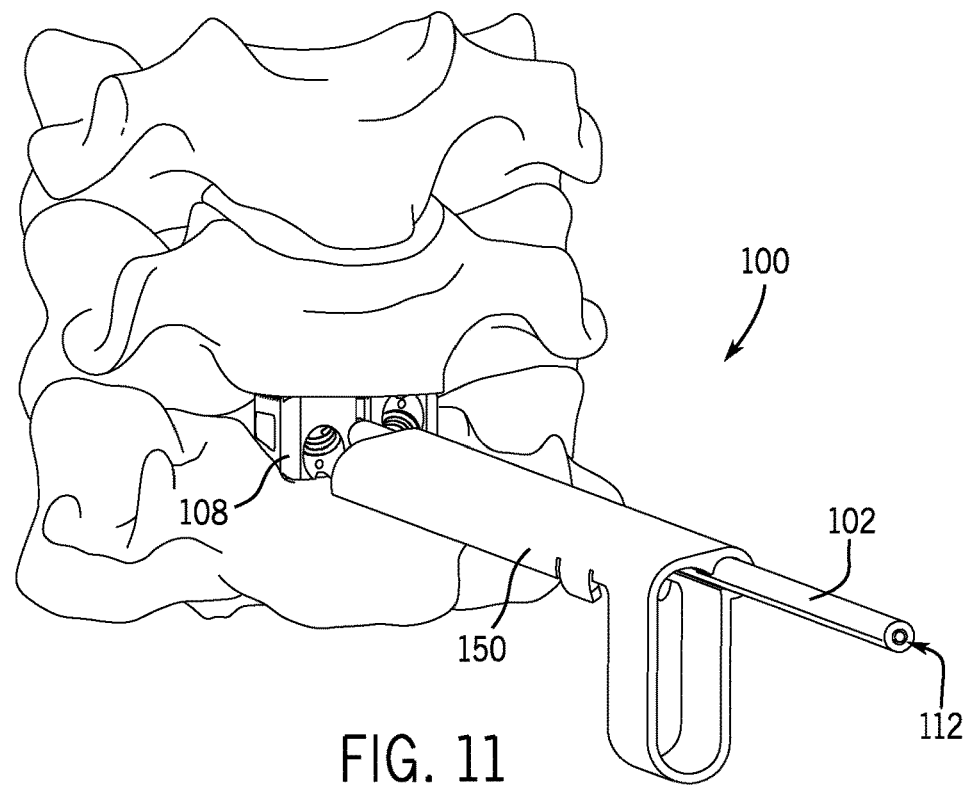
FIG. 11 is a perspective view of an additional delivery device in accordance with an embodiment of the present disclosure.
Figure 12:
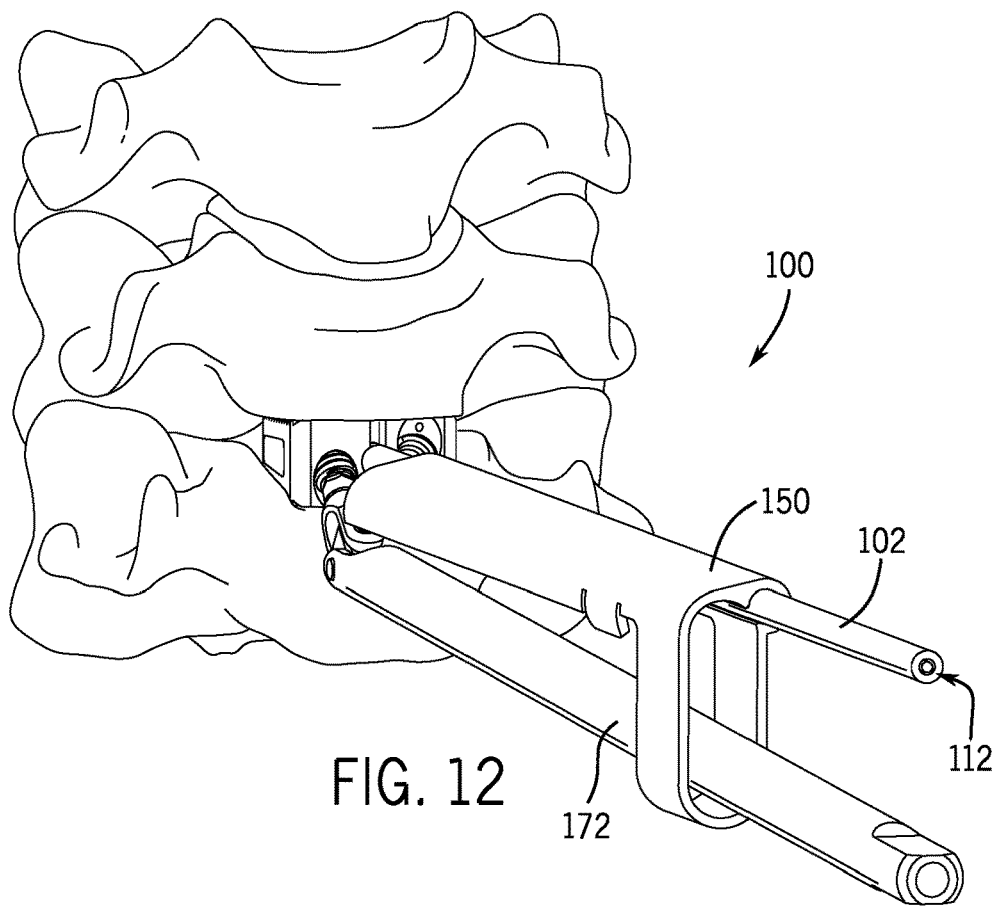
FIG. 12 is a perspective view of the delivery device of FIG. 11 shown with a drill or driver member connected thereto in accordance with an embodiment of the present disclosure.
Figure 13:
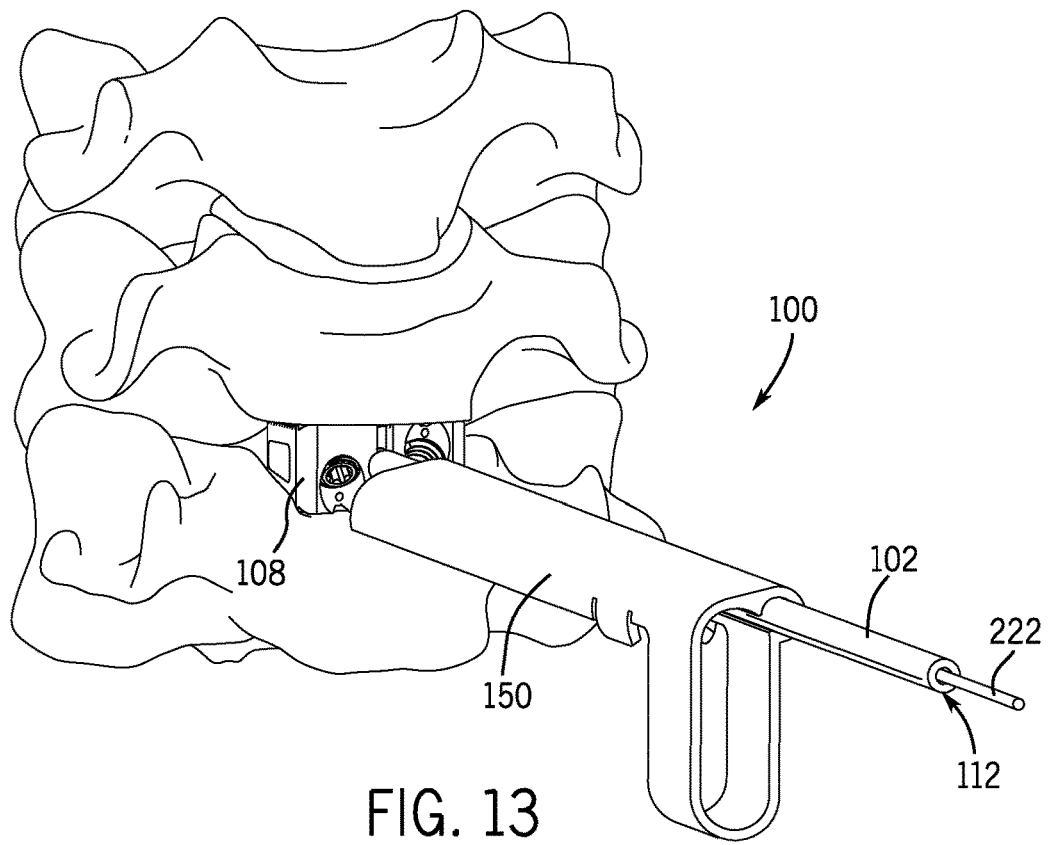
FIG. 13 is a perspective view of the delivery device of FIG. 11 shown with a guidewire connected thereto in accordance with an embodiment of the present disclosure.
Figure 14:
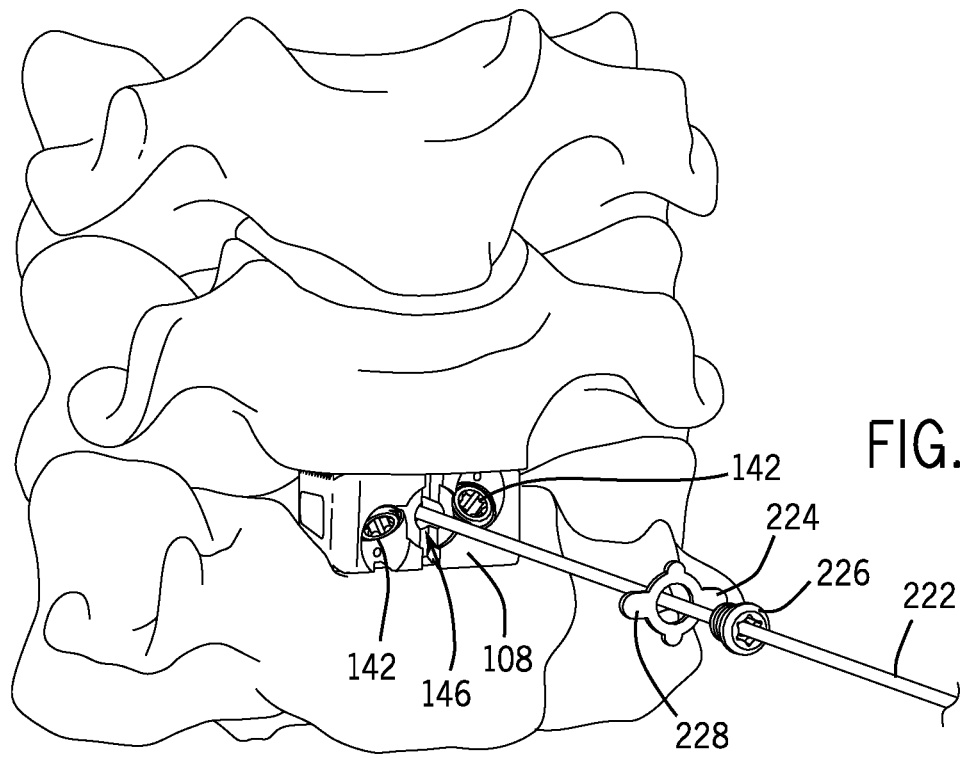
FIG. 14 is a perspective view of the delivery device of FIG. 13 with portions of the delivery device removed in accordance with an embodiment of the present disclosure.
Figure 15:
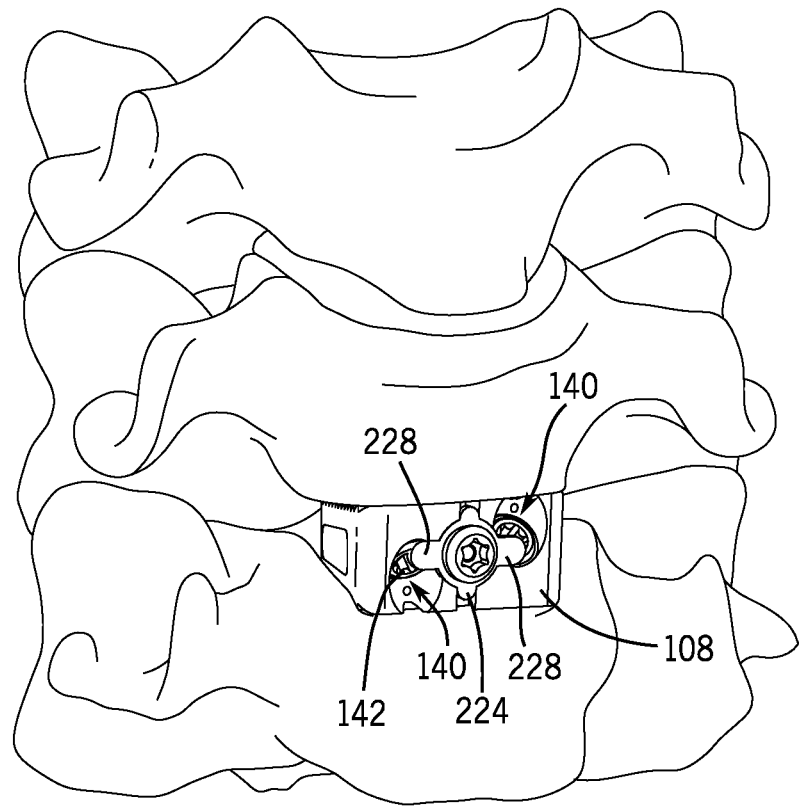
FIG. 15 is a perspective view of a fixation member attached to two adjacent vertebrae in accordance with an embodiment of the present disclosure.
Figure 16:
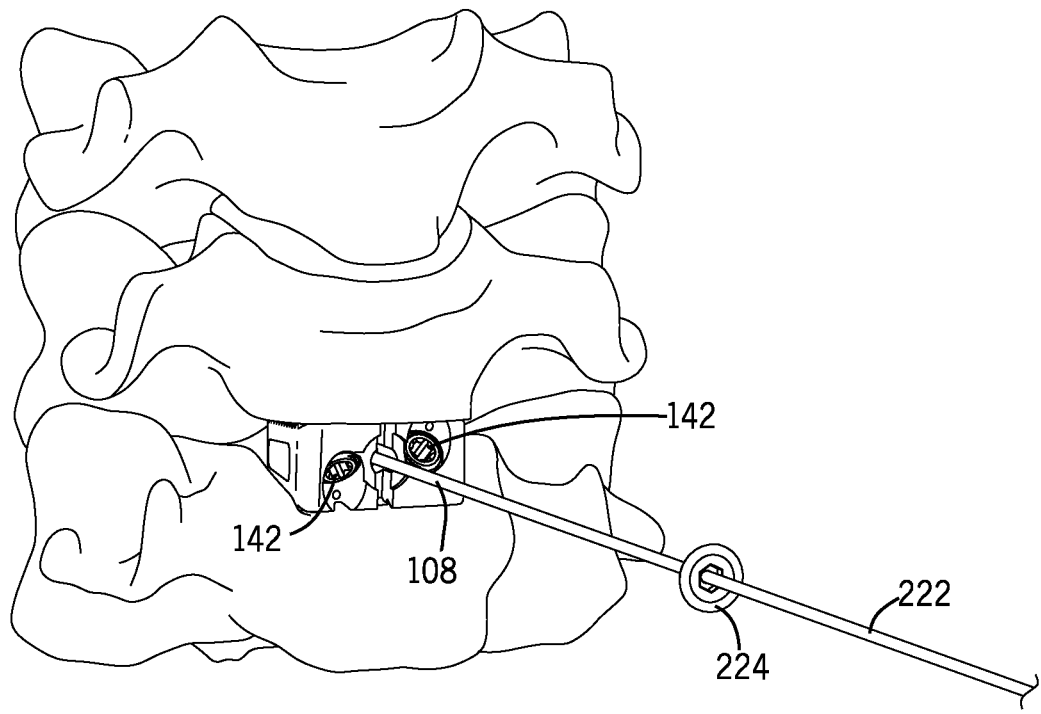
FIG. 16 is a perspective view of the delivery device of FIG. 14 shown with an additional back plate in accordance with an embodiment of the present disclosure.
Figure 17:
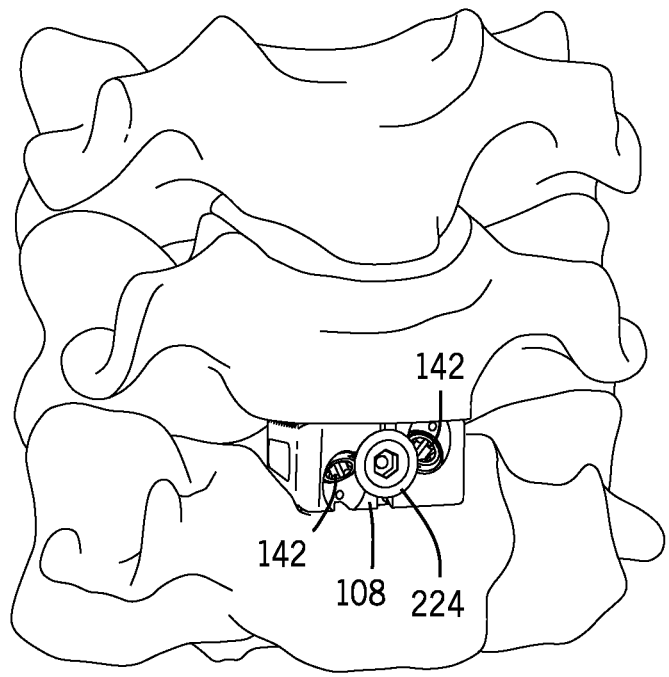
FIG. 17 is a perspective view of a fixation member attached to two adjacent vertebrae in accordance with an embodiment of the present disclosure.
Figure 18:
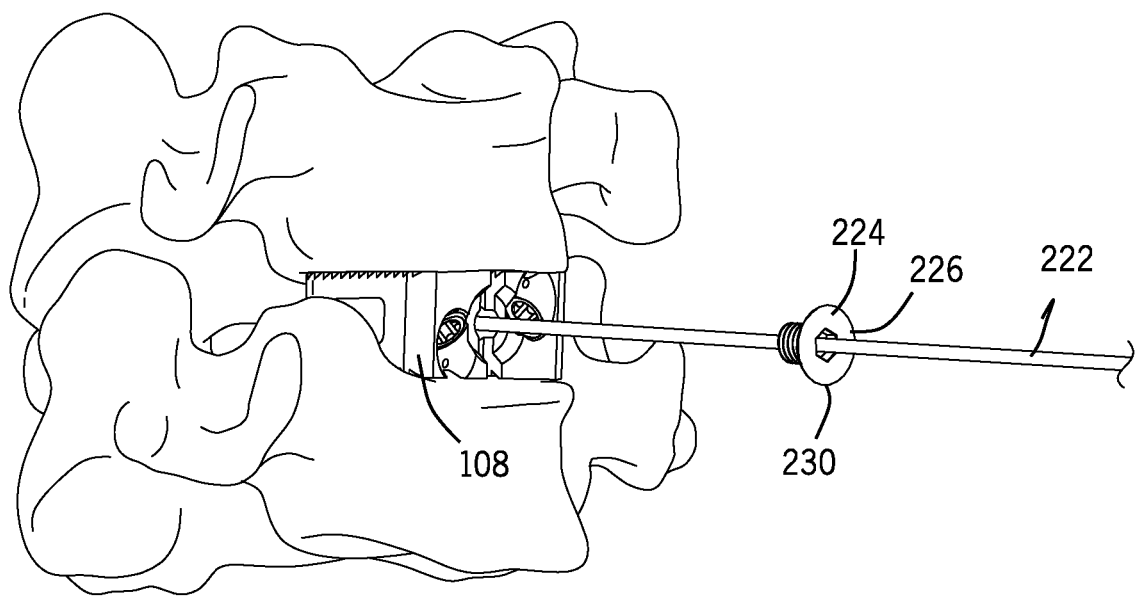
FIG. 18 is a perspective view of the delivery device of FIG. 14 shown with an additional back plate in accordance with an embodiment of the present disclosure.
Figure 19:
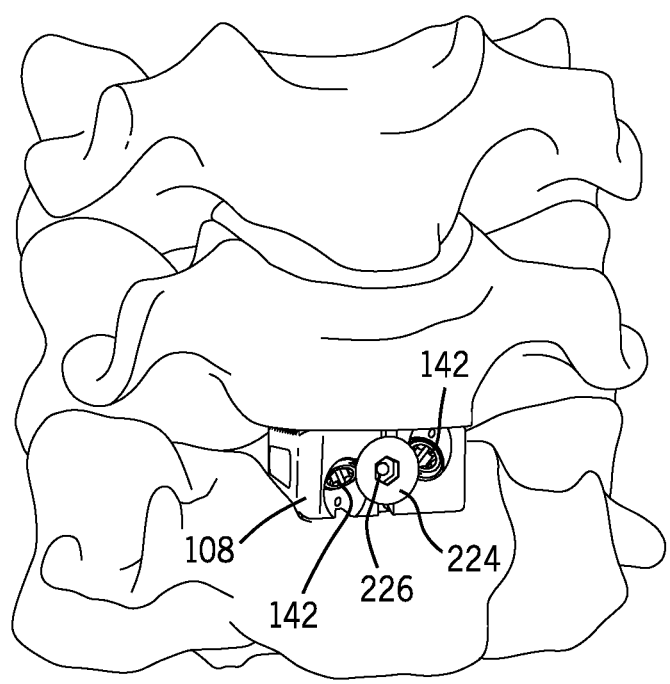
FIG. 19 is a perspective view of a fixation member attached to two adjacent vertebrae in accordance with an embodiment of the present disclosure.

In the embodiments described below, the anchor shaft 102 may be used as a primary portal and/or anchor for introduction of subsequent instruments in a screw delivery system 110. For example, as shown in the embodiments of FIGS. 11-13, the anchor shaft 102 may be hollow and include a central lumen or bore 112 through which one or more fixation devices and/or guide mechanisms may be advanced, as more fully described below. Additionally or alternatively, one or more fixation devices and/or guide mechanisms may be advanced over or around the anchor shaft 102 in some embodiments. Though shown as having a circular cross-section, the anchor shaft 102 may have substantially any cross-sectional shape, including without limitation square, elliptical, or triangular, among others. Furthermore, the anchor shaft 102 may be flexible or rigid depending on the desired characteristics of the delivery device 100.

Figure 27:
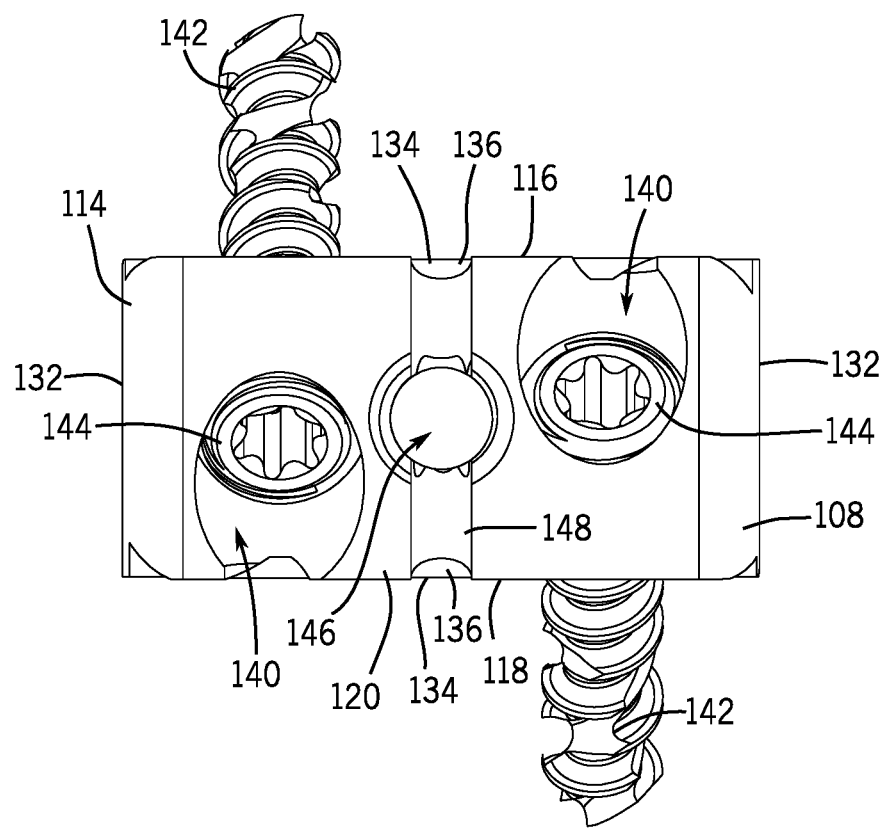
FIG. 27 is a front elevation view of a fixation member with bone screws inserted therein in accordance with an embodiment of the present disclosure.
Figure 28:
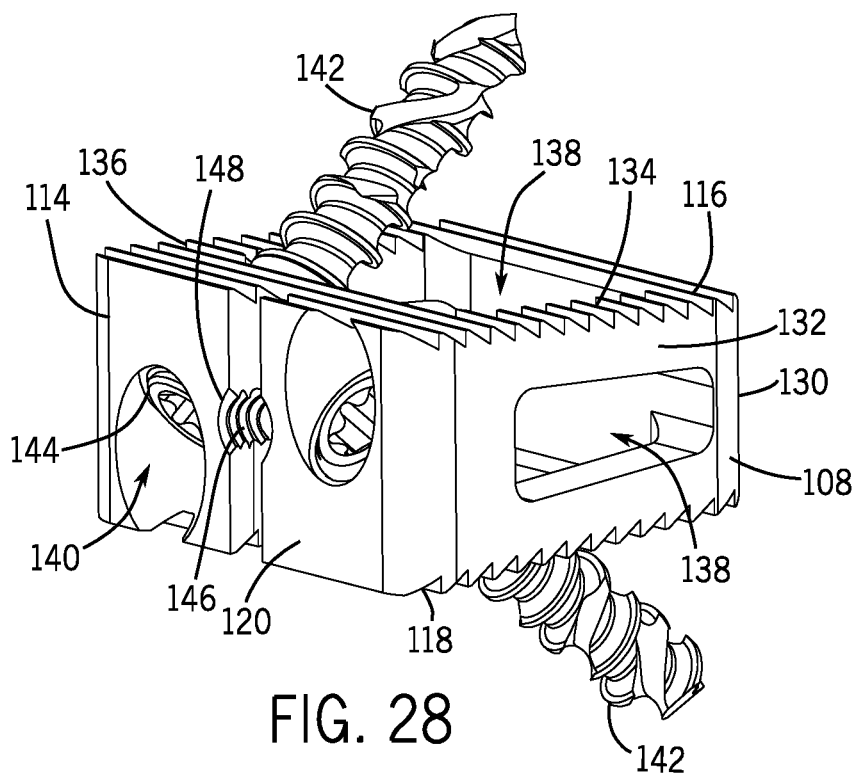
FIG. 28 is a perspective view of the fixation member of FIG. 27 in accordance with an embodiment of the present disclosure.
Figure 29:
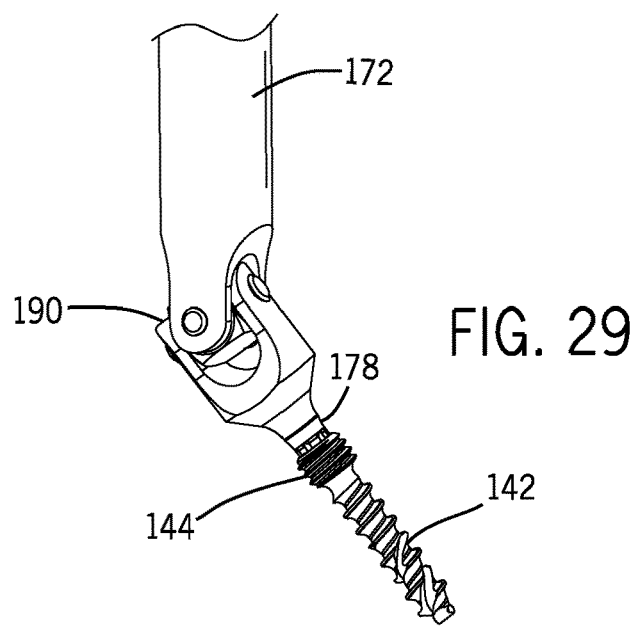
FIG. 29 is a side elevation view of a first end of a drill or driver member in accordance with an embodiment of the present disclosure.
Figure 30:
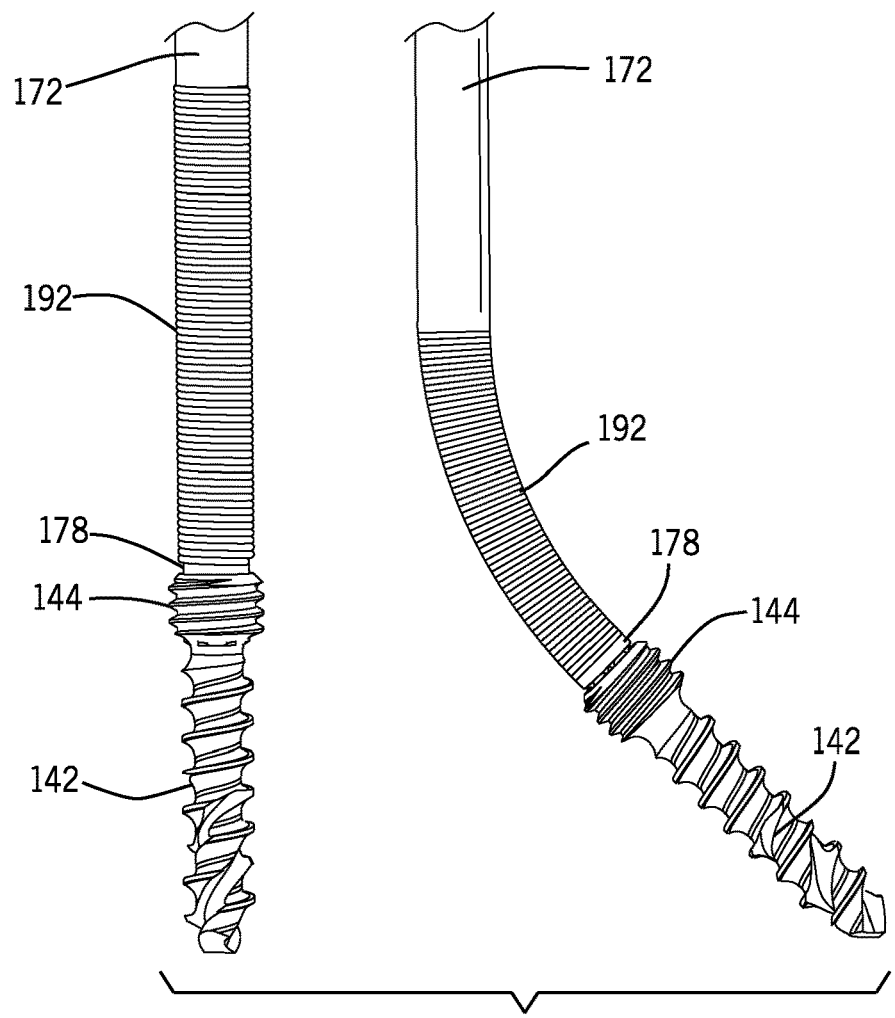
FIG. 30 is a side elevation view of a first end of an additional drill or driver member in accordance with an embodiment of the present disclosure.
Figure 31:
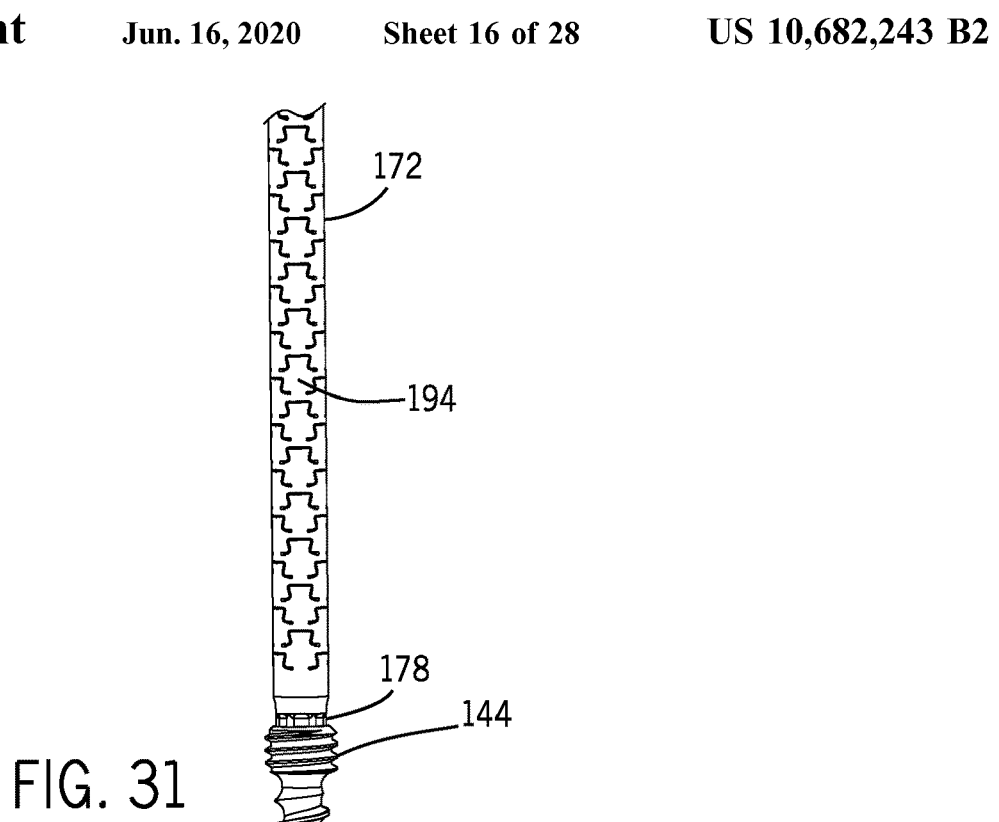
FIG. 31 is a side elevation view of a first end of an additional drill or driver member in accordance with an embodiment of the present disclosure.

With reference to FIGS. 1, 2, 27, and 28, the fixation member 108 may be sized and shaped to fit snugly (e.g., a friction fit) into or otherwise engage or abut adjacent vertebrae in a disc joint space between two adjacent vertebrae (see FIG. 2). As described herein, the fixation member 108 is operable to fixedly engage two adjacent vertebrae of a cervical spine (see FIG. 2) to fuse the two adjacent vertebrae together (e.g., C5 and C6 shown in FIG. 2). As best seen in FIGS. 27 and 28, the fixation member 108 includes a main body 114 defined by opposing top and bottom surfaces 116, 118, opposing front and rear surfaces 120, 130, and opposing side surfaces 132. The fixation member 108 may be generally cuboid in shape and may include engagement features to retain the fixation member 108 fixedly within the disc joint space. For example, the top and bottom surfaces 116, 118 may include a plurality of directional projections 134 that allow the fixation member 108 to be inserted into a disc space but also limit its removal. For instance, the projections 134 may be shaped to resemble a sawtooth waveform in cross-section (see FIG. 28), with vertical sections 136 of the projections 134 facing towards the front surface 120. As best seen in FIG. 28, the projections 134 may be horizontally spaced (e.g., in uniform rows) and may extend substantially between the opposing side surfaces 132 of the main body 114. To reduce weight and offer cross sectional areas for bone bridging, the fixation member 108 may include a plurality of cavities 138 defined in the surfaces of the fixation member 108 (e.g., the opposing top and bottom surfaces 116, 118 and the opposing side surfaces 132). In some embodiments, the cavities 138 may interconnect such that the main body 114 may be considered hollow. The fixation member may be made of bone or bone substitute material or a biocompatible metal, ceramic, polymer, or some combination thereof. Examples include metals such as titanium, stainless steel, cobalt chrome, chro-moly and polymers such as Polycarbonate, PEI, UHMW PE, ABS, PEEK etc.

With continued reference to FIGS. 1, 2, 27, and 28, the fixation member 108 may include securement features to fixedly secure the fixation member 108 within an intervertebral joint or disc joint. For instance, a plurality of securement apertures 140 (e.g., two securement apertures 140) may be formed in at least the front surface 120 of the fixation member 108. As illustrated in the embodiments of FIGS. 27 and 28, the securement apertures 140 may be sized to receive a respective bone screw 142 (e.g., a ALLY™ Bone Screw-L from Providence Medical Technology, Inc.) therein. In some embodiments, the securement apertures 140 may be sized such that screw heads 144 of the bone screws 142 are positioned entirely within the securement apertures 140 or lie at most flush with the front surface 120 of the fixation member 108. In addition, the securement apertures 140 may be angled so the bone screws 142 extend through the opposing top and bottom surfaces 116, 118 of the fixation member 108 to engage cervical vertebrae. In some embodiments, at least one of the securement apertures 140 may be angled such that a bone screw 142 inserted therein extends upwardly to engage an upper vertebra. In such embodiments, at least one of the other securement apertures 140 may be angled such that a bone screw 142 inserted therein extends downwardly to engage a lower vertebra. In each of the embodiments described above, the bone screws 142 may extend through the cavities 138 defined in the top and bottom surfaces 116, 118 of the main body 114. As seen in FIGS. 27 and 28, the fixation member 108 includes an anchor cavity 146 defined in the front surface 120 (e.g., in a center portion 148 of the front surface 120) to secure the fixation member 108 to the anchor shaft 102. In such embodiments, the delivery device 100 guides the fixation member 108 to a spine with the rear surface 130 of the fixation member 108 projecting into a disc space first. As shown, the anchor cavity 146 may be threaded to receive corresponding threads of the anchor shaft 102. The bone screw may be made of metals such as titanium, stainless steel, cobalt chrome, chro-moly or polymers such as Polycarbonate, PEI, UHMW PE, ABS, PEEK, etc.

Figure 3:
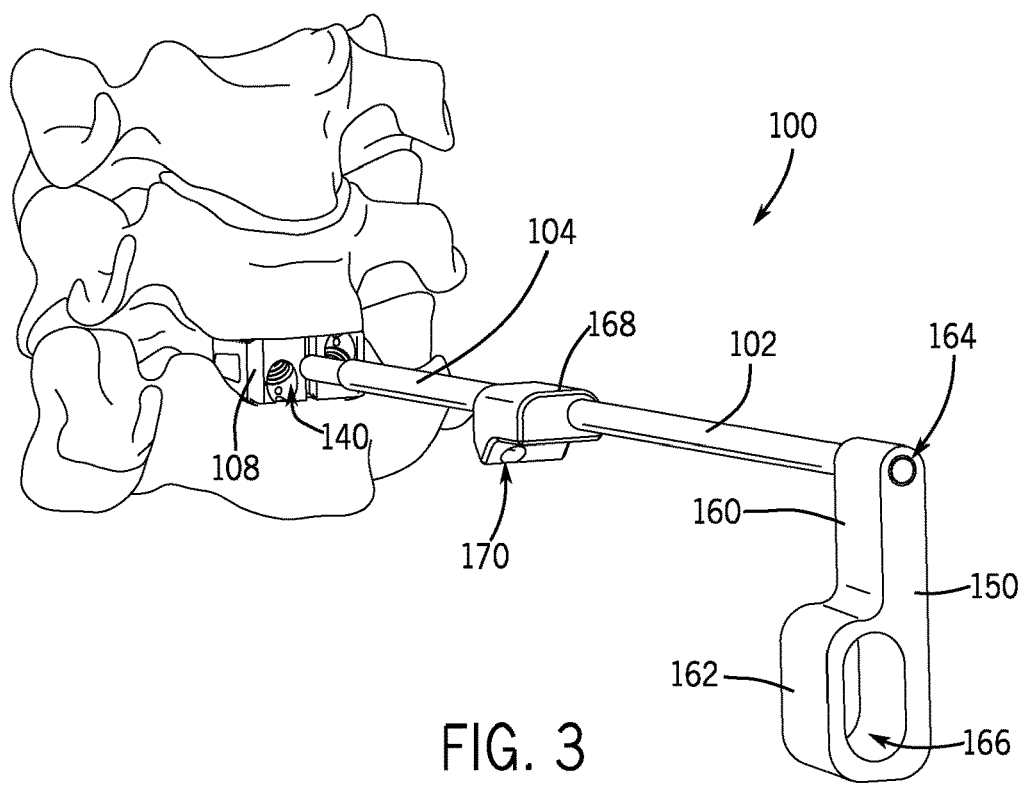
FIG. 3 is a perspective view of an additional delivery device in accordance with an embodiment of the present disclosure.
Figure 4:
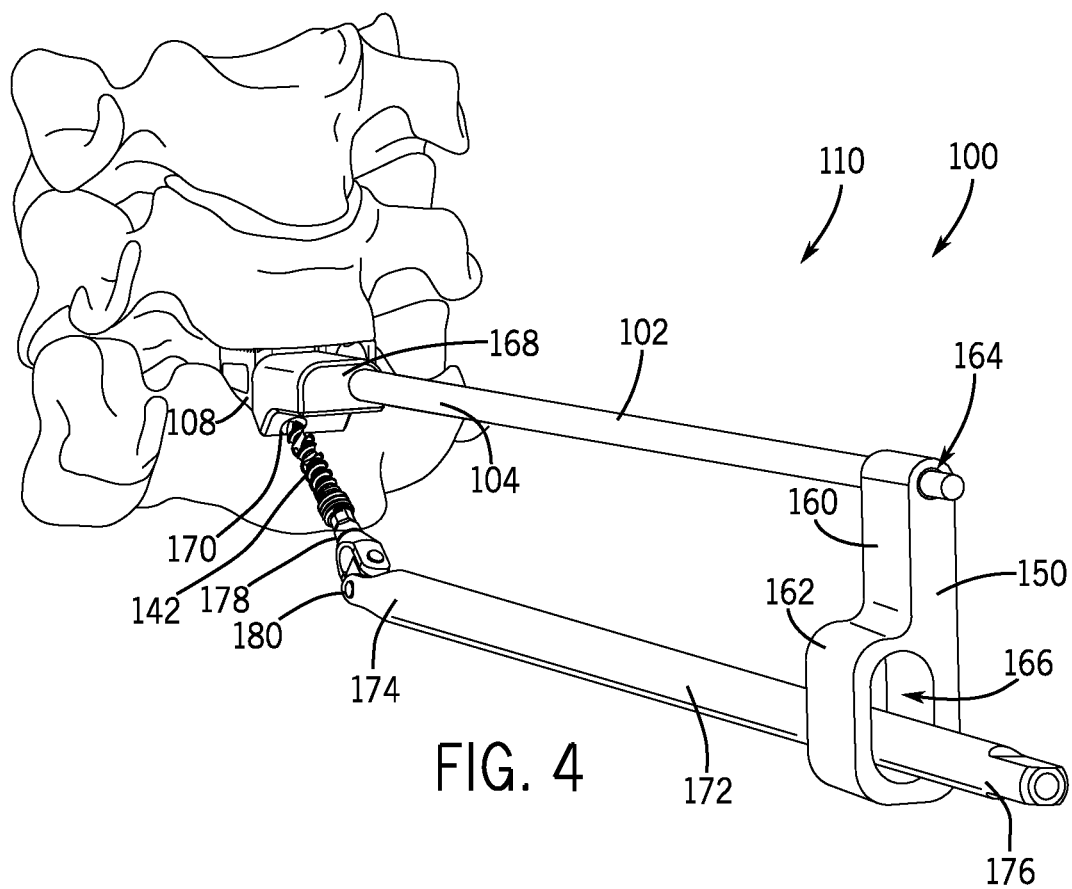
FIG. 4 is a perspective view of the delivery device of FIG. 3 shown with a drill or driver member connected thereto in accordance with an embodiment of the present disclosure.

With reference to FIGS. 3 and 4, the delivery device 100 may include a guide member 150 operably associated with the anchor shaft 102 to direct other tools of spinal instrumentation in relation to the anchor shaft 102 and/or fixation member 108. For ease of use during surgery, the guide member 150 may be slidably coupled with the anchor shaft 102 and may rotate about the anchor shaft 102 to position the guide member 150 in substantially any position relative to the anchor shaft 102. In the embodiment of FIGS. 3 and 4, the guide member 150 includes a first portion 160 and a second portion 162, the first portion 160 being connected to the anchor shaft 102 and positioned between the anchor shaft 102 and the second portion 162. Each of the first and second portions 160, 162 may be cannulated to include a first lumen 164 and a second lumen 166, respectively. As shown, the first lumen 164 is sized to bear rotatably and slidably against the anchor shaft 102. The second lumen 166, which may be referred to as a drill path, may be larger in diameter than, and may be laterally offset from, the first lumen 164. In some embodiments, the second lumen 166 may be elliptical to allow a spinal instrumentation tool inserted therein to move vertically within the second lumen 166 within a defined range of motion. For example, the second lumen 166 may substantially surround the spinal instrument tool (e.g., a drill) and may be sized and shaped to limit movement of the tool within a plane offset and extending parallel to a vertical plane defined by the anchor shaft 102.

With continued reference to FIGS. 3 and 4, in some embodiments, the delivery device 100 may include a screw guide 168 operably connected to the anchor shaft 102 to direct the bone screw 142 for insertion in the fixation member 108. In one embodiment, the screw guide 168 is cannulated and may be placed over the anchor shaft 102 and directed towards the distal portion 104 of the anchor shaft 102 and adjacent the fixation member 108. The screw guide 168 may include one or more angled lumen 170 to define a trajectory for bone screw insertion. In various embodiments, the angled lumen 170 of the screw guide 168 may be formed as part of the screw guide or may be removable. For example, when the screw guide 168 is positioned adjacent the fixation member 108 (i.e., "docked"), the angled lumen 170 may be concentric with at least one securement aperture 140 of the fixation member 108. Once docked against the fixation member 108, the angled lumen 170 of the screw guide 168 directs the bone screw 142 into proper alignment with the fixation member 108. In some embodiments, the angled lumen 170 may be offset from the cannulated portion of the screw guide 168 and may lie within the plane defined by the second lumen 166.

As illustrated in FIG. 4, in an exemplary embodiment, the screw delivery system 110 may include a drill or driver member 172 to both advance the bone screw 142 towards the fixation member 108 and drive the bone screw 142 into the fixation member 108 and into an adjacent vertebra. The drill or driver member 172 may be an elongated shaft and may include a first end 174 and a second end 176 extending from the first end 174. Like the anchor shaft 102, the drill or driver member 172 may be a solid shaft or a cannulated tube (see FIG. 6) and may be generally long enough to extend from the first end 174 to a location outside a patient, where at least a portion of the drill or driver member 172 (e.g., the second end 176) can be held and manipulated by a surgeon. In some embodiments, the drill or driver member 172 may be slidably coupled with the guide member 150 (e.g., through the drill path or second lumen 166) adjacent the anchor shaft 102. In such embodiments, the offset nature of the second lumen 166 may position the drill or driver member 172 in substantial alignment with the offset angled lumen 170 of the screw guide 168. In some embodiments, the drill path or second lumen 166 may be sized so the drill or driver member 172 can articulate to the desired angular approach to drive the bone screw 142 into place. Once the bone screw 142 is driven within one of the securement apertures 140 of the fixation member 108 by the drill or driver member 172, the screw guide 168, the guide member 150, and/or the drill or driver member 172 may be rotated about the anchor shaft 102 (e.g., 180 degrees about the anchor shaft 102) to repeat the process for subsequent bone screw insertion in other securement apertures 140, if any, of the fixation member 108.

Figure 32:
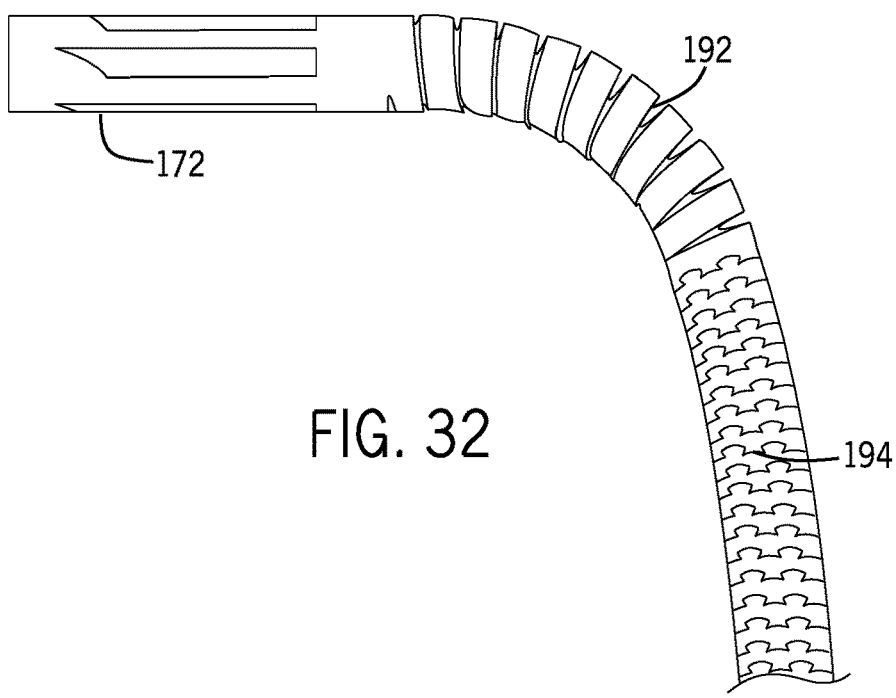
FIG. 32 is a side elevation view of a first end of an additional drill or driver member in accordance with an embodiment of the present disclosure.

With reference to FIGS. 4 and 29-32, for instance, the drill or driver member 172 may be operable to releasably grip the bone screw 142 until the bone screw 142 is driven into position within a disc joint space. For example, the first end 174, which may include a bit 178 for corresponding driving engagement with the screw head 144 of the bone screw 142 (see FIG. 26), may releasably retain the bone screw 142 through friction fit, interference fit, temporary attachment means, or other temporary securement mechanisms. In some embodiments, the first end 174 may flex, bend, or articulate in relation to the second end 176 to allow proper alignment of the bone screw 142 within the screw guide 168 and the fixation member 108. For instance, the first end 174 may include a coupling 180 that permits the drill or driver member 172 to rotate and articulate with the bone screw 142 at a specified angle. In some embodiments, the specified angle is between 30 and 70 degrees from collinear to the anchor shaft 102. As one example, the coupling 180 may take the form of a universal joint 190 that permits offset rotation of the first end 174 in relation to the second end 176 of the drill or driver member 172 (see FIG. 29). In other examples, the coupling 180 may be a resiliently deformable coil spring 192 that is capable of transmitting torque to the bone screw 142 at a desired angular trajectory (see FIG. 30). As yet another example, the coupling 180 may be a laser cut tube portion 194 that resiliently deforms to a desired angular trajectory (see FIGS. 31 and 32). Although three exemplary embodiments are shown in FIGS. 29-32, the coupling 180 may include other deformable mechanisms, including without limitation any combination of the three examples discussed above (see, e.g., FIG. 32 showing a coil spring 192 and a laser cut tube portion 194).

Figure 5:
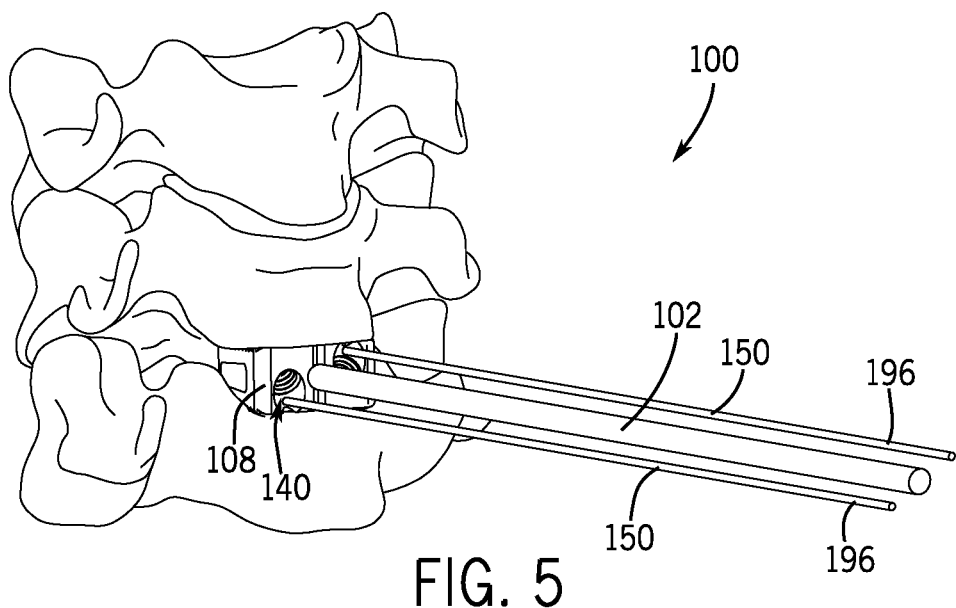
FIG. 5 is a perspective view of an additional delivery device in accordance with an embodiment of the present disclosure.
Figure 6:
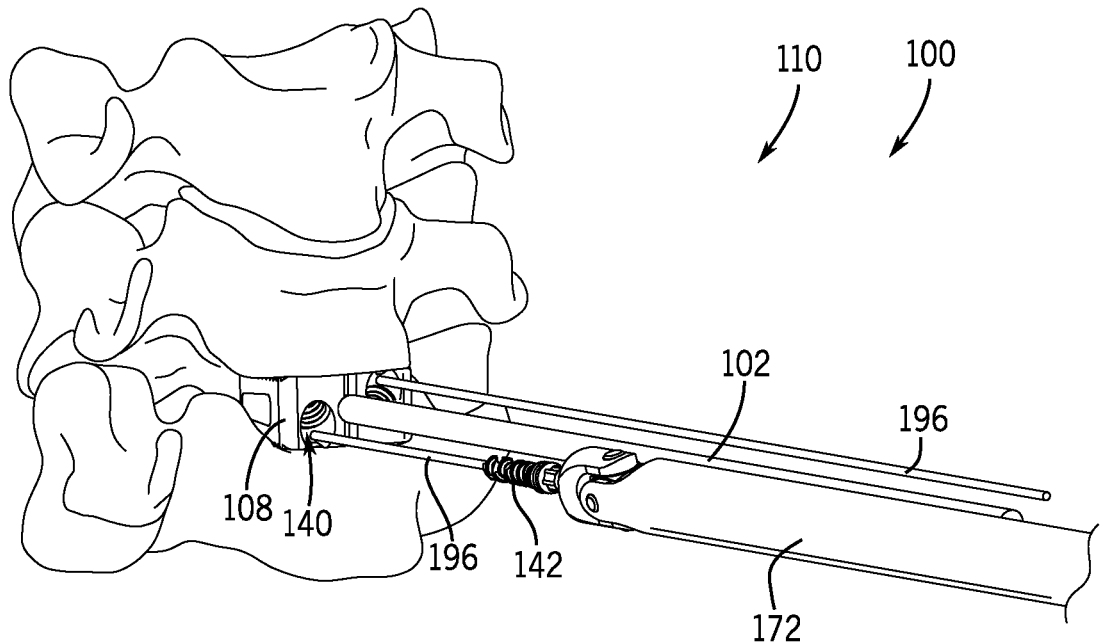
FIG. 6 is a perspective view of the delivery device of FIG. 5 shown with a drill or driver member connected thereto in accordance with an embodiment of the present disclosure.
Figure 7:
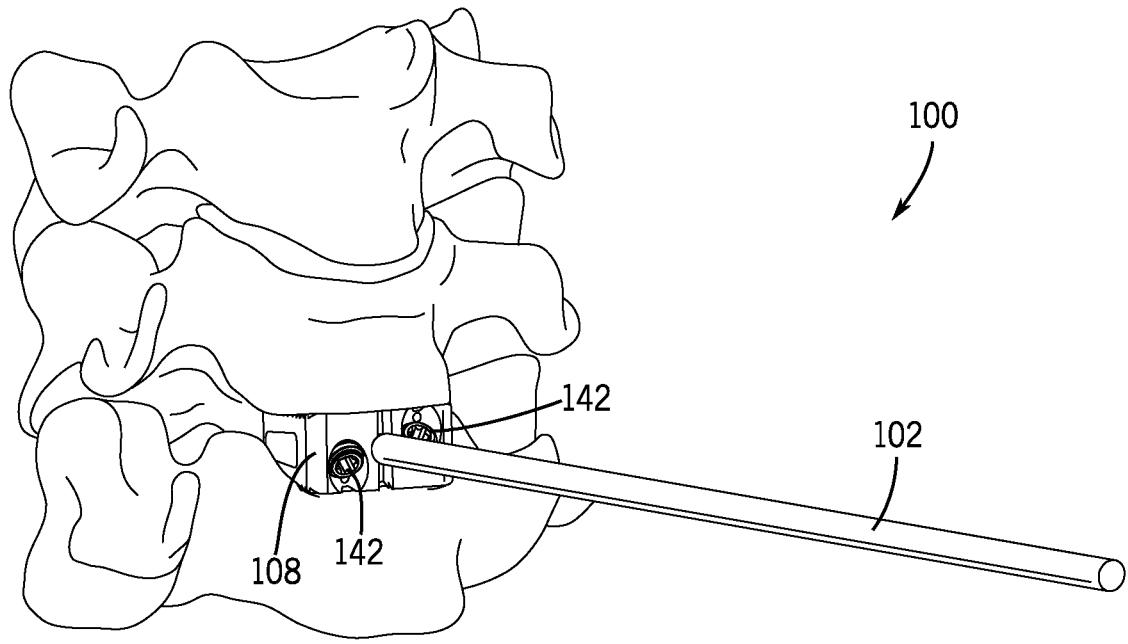
FIG. 7 is a perspective view of the delivery device of FIG. 5 with portions of the device removed in accordance with an embodiment of the present disclosure.
Figure 8:
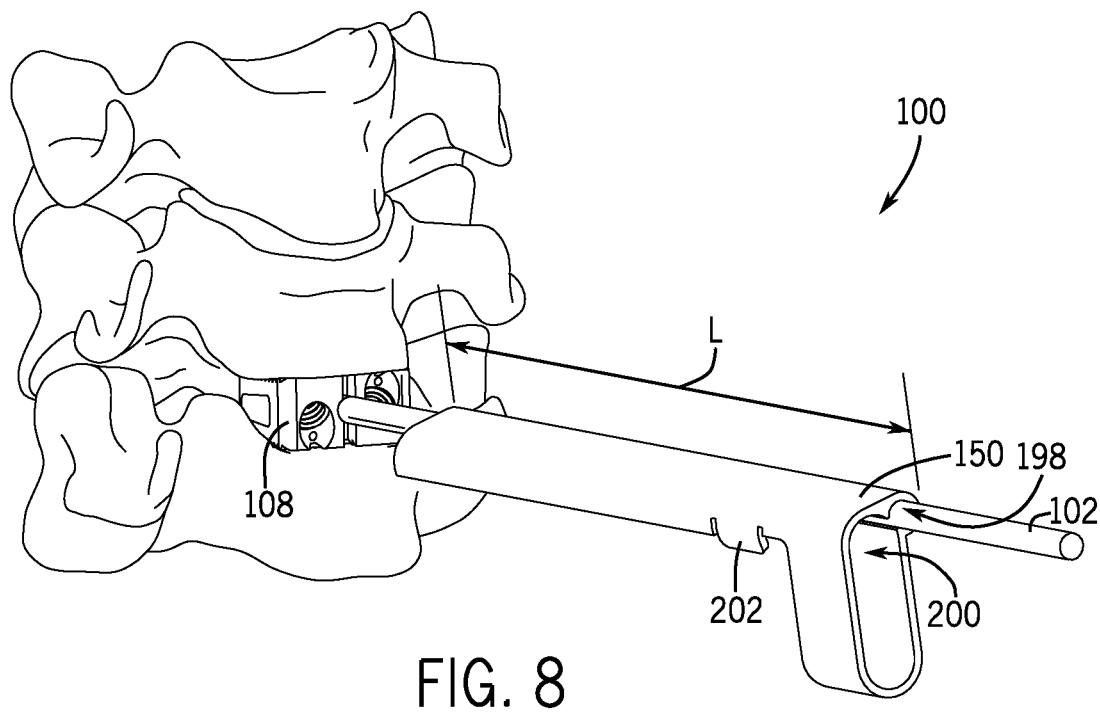
FIG. 8 is a perspective view of an additional delivery device in accordance with an embodiment of the present disclosure.
Figure 9:
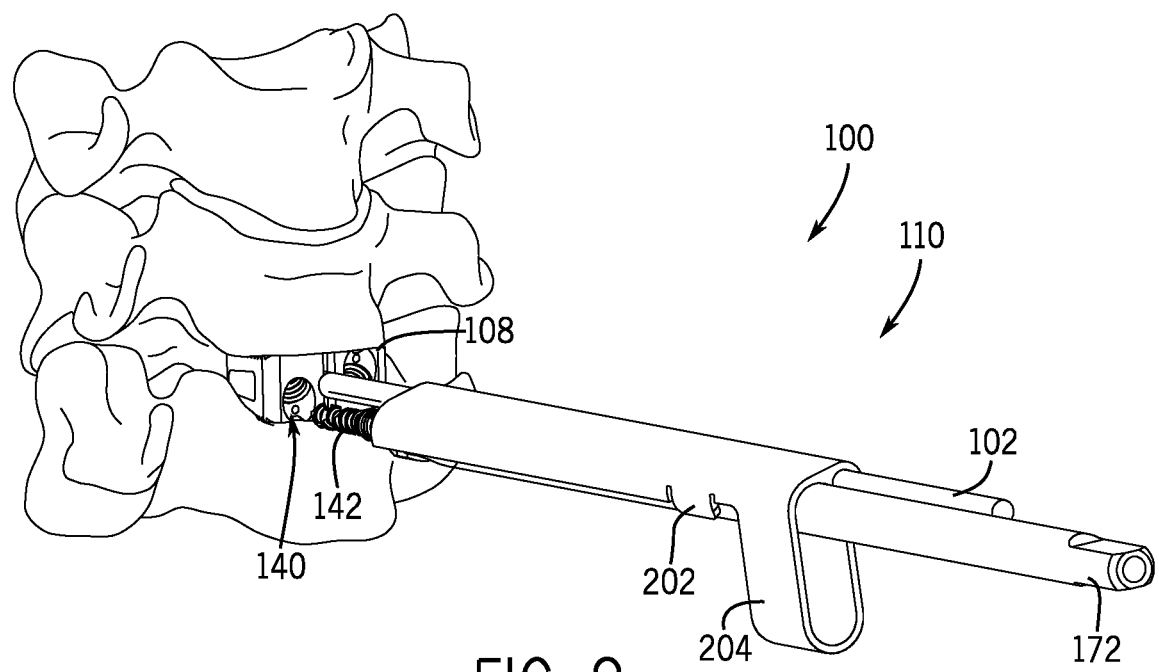
FIG. 9 is a perspective view of the delivery device of FIG. 8 shown with a drill or driver member connected thereto in accordance with an embodiment of the present disclosure.

Referring now to FIGS. 5-7, in another embodiment, the guide member 150 may take the form of one or more guidewires 196 extending adjacent and parallel to the anchor shaft 102. In such embodiments, each guidewire 196 may be docked or anchored onto the fixation member 108 (e.g., by threading engagement) to set a trajectory for bone screw insertion. As shown, each guidewire 196 may be anchored within the securement aperture(s) 140 of the fixation member 108, though other anchor locations are contemplated. As shown in FIG. 6, cannulated bone screw 142 and drill member 172 are positioned over one of the guidewires 196 and advanced towards the respective securement aperture 140 of the fixation member 108. Once the cannulated bone screw 142 is docked against the fixation member 108, the guidewire 196 is removed, and the bone screw 142 is torqued into position by the drill or driver member 172. Should the bone screw 142 and the drill or driver member 172 decouple, the guidewire 196 may be used to reposition the bone screw 142 on the drill or driver member 172.

With reference now to FIGS. 8-10C, in one embodiment, the guide member 150 may be single (not shown) or double cannulated and include a length L sufficient to preset the trajectories of the drill or driver member 172 and the bone screw 142. For example, the guide member 150 may include a first cannula 198 and a second cannula 200 extending parallel to the first cannula 198, each of the first and second cannulas 198, 200 being partially or fully enclosed. In some embodiments, the first and second cannulas 198, 200 are sized and shaped to slidably receive the anchor shaft 102 and the drill or driver member 172, respectively. The second cannula 200 may include one or more release tabs 202 to releasably retain the drill or driver member 172 in a desired angular relationship with the anchor shaft 102 (e.g., substantially parallel) to efficiently dock the bone screw 142 within the securement apertures 140 of the fixation member 108, for example. As shown in FIG. 10A, once a portion of the bone screw 142 has been inserted within the securement aperture 140, the drill or driver member 172 may be disengaged from the second cannula 200 to articulate to the desired angular approach as the bone screw 142 is driven into place. In some embodiments, the range of motion of the drill or driver member 172 may be limited or defined by a ring 204 extending below the guide member 150. As shown, the ring 204 substantially surrounds the drill or driver member 172 and may be sized and shaped to limit movement of the drill or driver member 172 within a plane offset and extending parallel to a vertical plane defined by the anchor shaft 102.

Figure 10A:
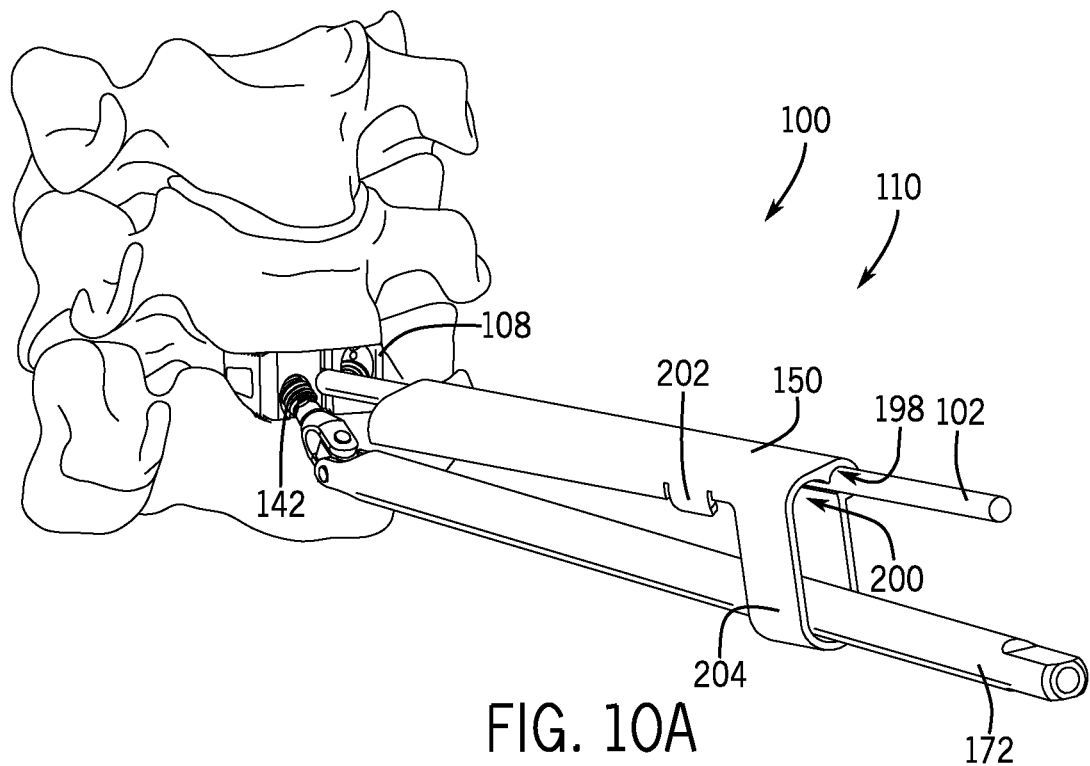
FIG. 10A is a perspective view of the delivery device of FIG. 9 in accordance with an embodiment of the present disclosure.
Figure 10B:
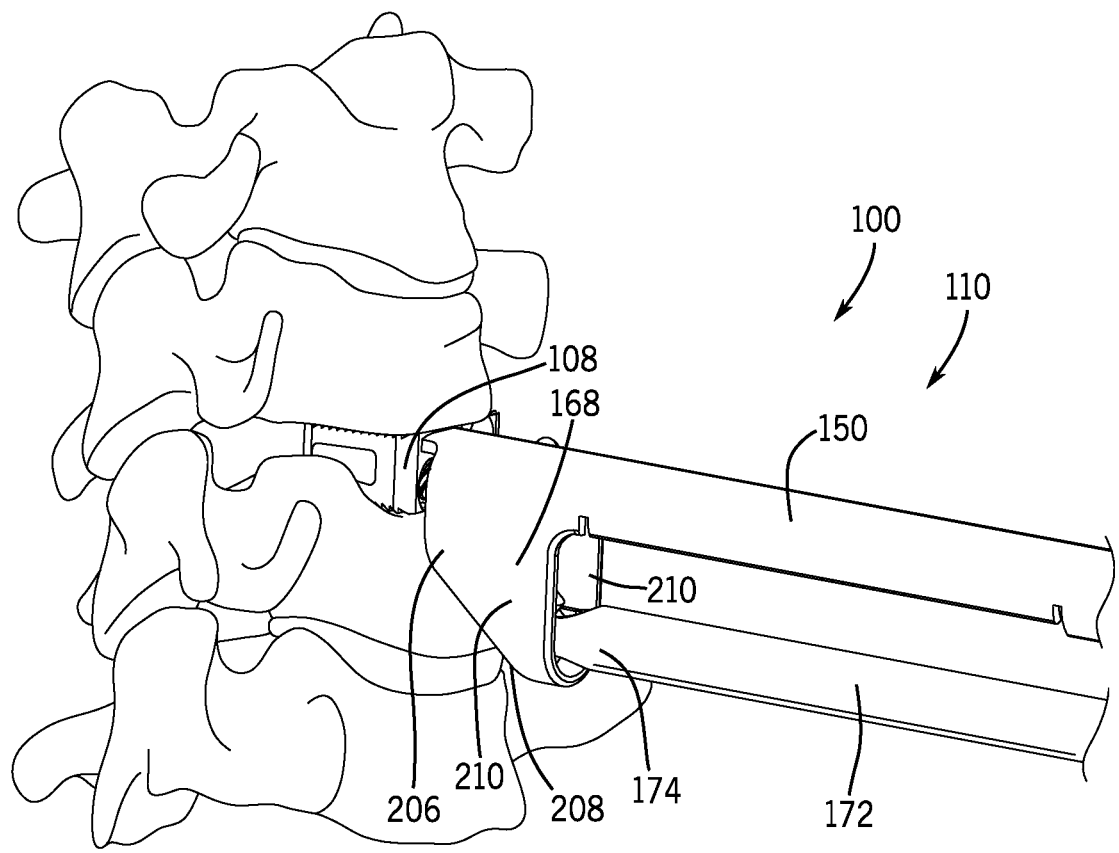
FIG. 10B is a lateral view of the delivery device of FIG. 10A shown with a screw guide connected thereto in accordance with an embodiment of the present disclosure.
Figure 10C:
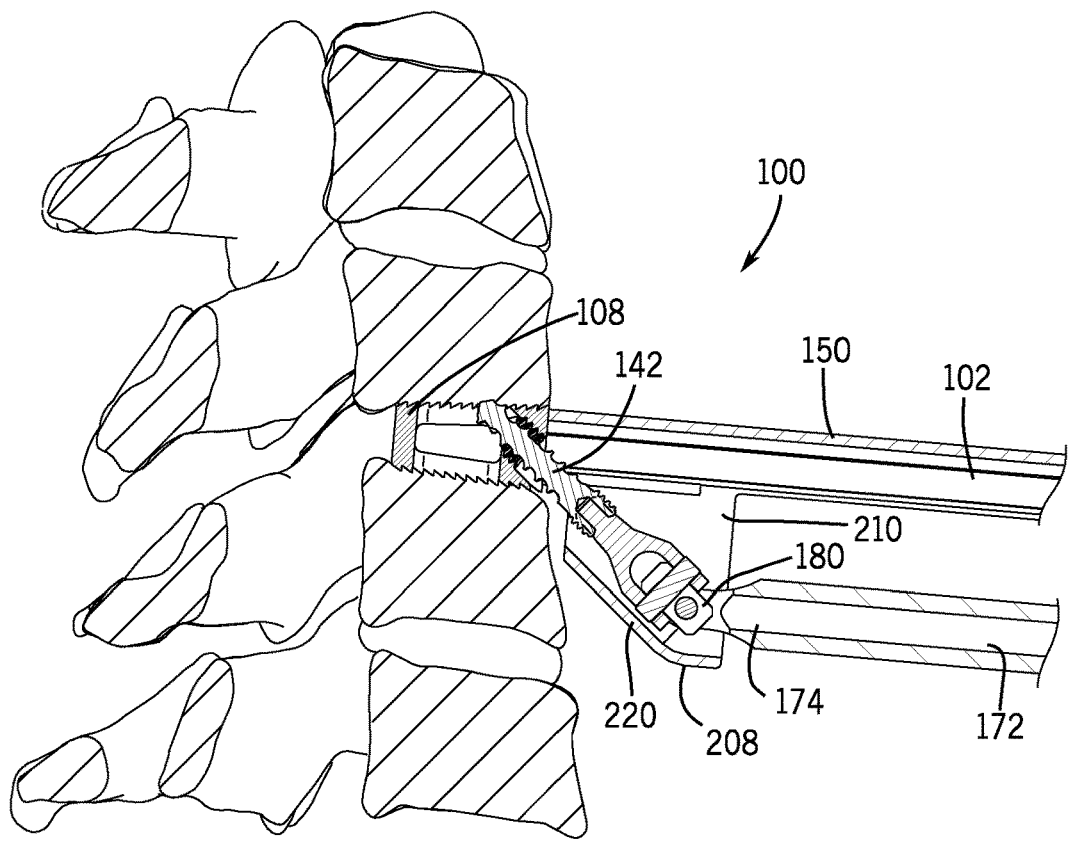
FIG. 10C is a cross-sectional view of the delivery device of FIG. 10B in accordance with an embodiment of the present disclosure.

With reference to FIGS. 10B and 10C, in some embodiments, the screw guide 168 and the guide member 150 may be formed as a single piece, or monolithically or integrally together. The screw guide 168 may support both the bone screw 142 and the drill or driver member 172 at a desired angle to insert the bone screw 142 into the fixation member 108. In some embodiments, the screw guide 168 may include a cage 206 attached to the guide member 150, the cage 206 defined at least partially by a bottom wall 208 and opposing side walls 210 extending from the bottom wall 208 to the guide member 150. To set the trajectory of the bone screw 142 to the desired angle, the bottom wall 208 may include an angled surface 220 that extends towards the fixation member 108 at least when the screw guide 168 is docked against the fixation member 108 (see FIG. 10C). As shown, during insertion of the bone screw 142 into the fixation member 108, the bottom wall 208 may support the first end 174 of the drill or driver member 172 (e.g., the coupling 180).

Referring to FIGS. 11-19, in some embodiments, the anchor shaft 102 may be cannulated to receive a guidewire 222 therein for anchoring of subsequent spinal instrumentation tools or fasteners (see FIG. 13). For example, as shown in FIG. 13, the guidewire 222 may be inserted within the bore 112 of the cannulated anchor shaft 102 and docked against the fixation member 108 to maintain position while the delivery device 100 is removed. Keeping the guidewire 222 in place, both a back plate 224 and a cannulated fastener 226 may be advanced towards the fixation member 108 and threaded into the anchor cavity 146 to secure the bone screw(s) 142 further in place (see FIG. 14). As shown in at least FIG. 15, the back plate 224 may include a diameter such that the back plate 224 extends at least partially over the securement apertures 140 of the fixation member 108. By covering the securement apertures 140 either fully or partially, the back plate 224 may be operable to inhibit or at least limit the bone screw(s) 142 from backing out, thus decreasing the need for subsequent surgery and/or the level of post-operative care. Furthermore, use of a back plate 224 may eliminate the need to have a fixation member 108 with mating threads for the bone screw 142, thus giving the bone screw 142 greater freedom while being driven into bone and/or tissue. In some embodiments, the back plate 224 may define one or more tabs 228 that extend at least partially over the securement aperture(s) 140 (see FIG. 15, 16). In another embodiment, the back plate 224 may be non-oriented, thus limiting the need to precisely align the back plate 224 against the fixation member 108 (see FIGS. 17 and 19). Additionally or alternatively, the cannulated fastener 226 may include an oversized head 230 to effectively cover the securement aperture(s) 140 and prevent back out of the bone screw(s) 142 (see FIGS. 18 and 19).

Figure 20:
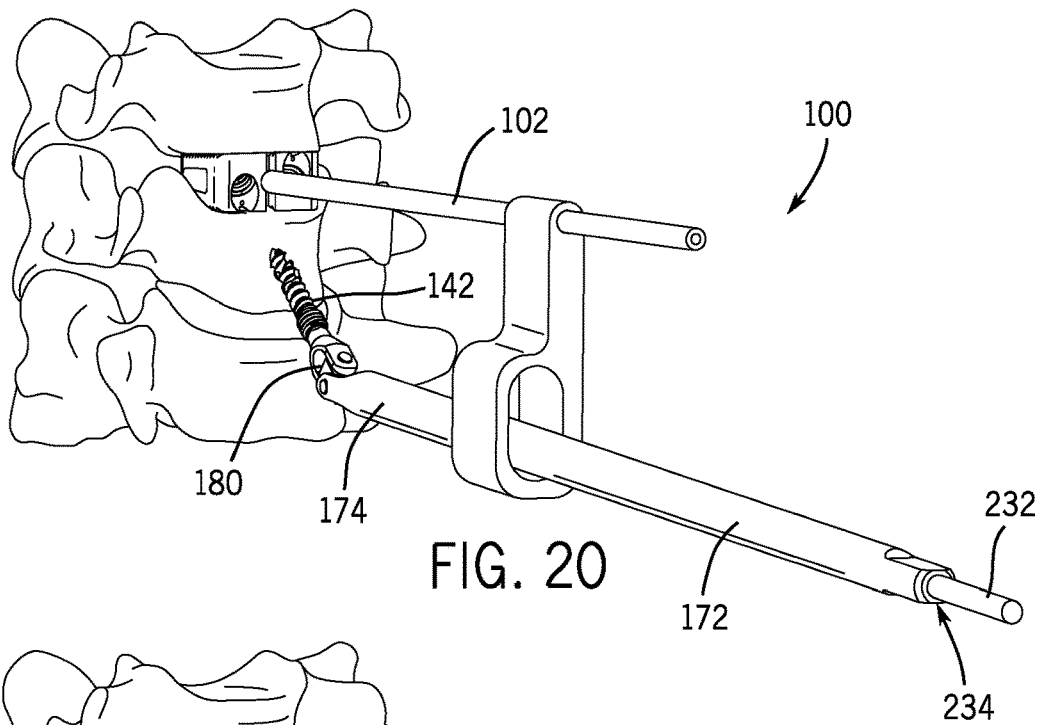
FIG. 20 is a perspective view of an additional delivery device in accordance with an embodiment of the present disclosure.
Figure 21:
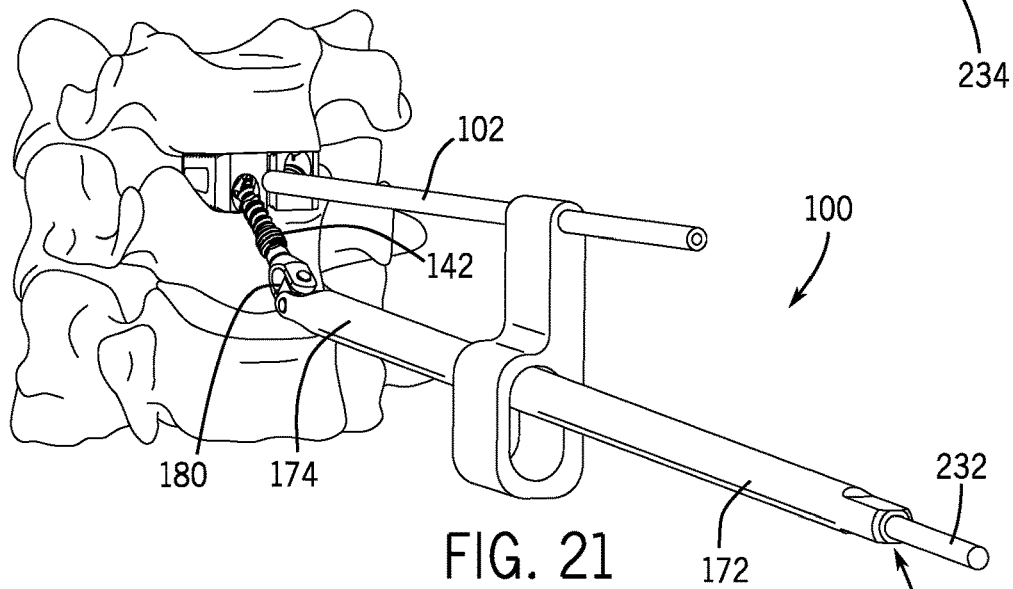
FIG. 21 is a perspective view of the delivery device of FIG. 20 in accordance with an embodiment of the present disclosure.
Figure 22:
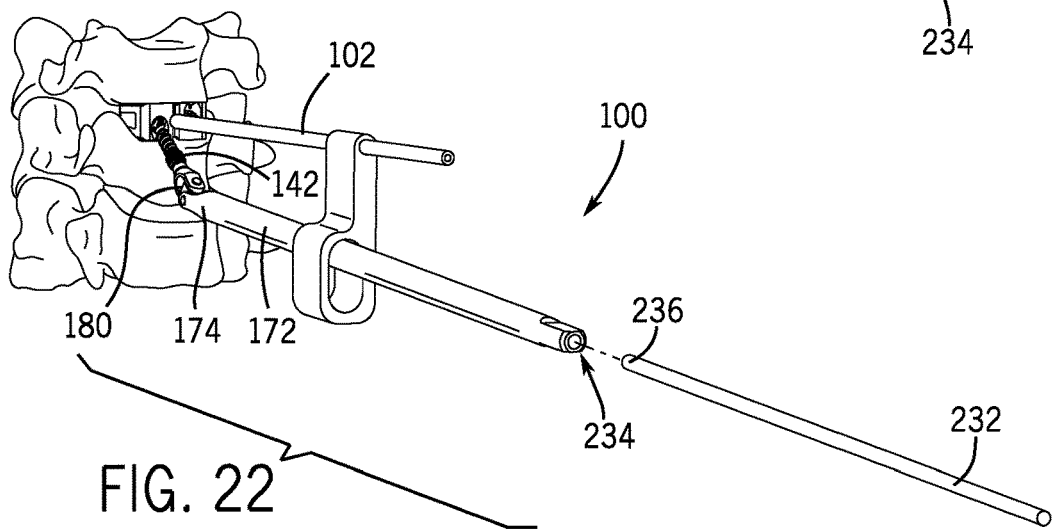
FIG. 22 is a perspective view of the delivery device of FIG. 20 in accordance with an embodiment of the present disclosure.
Figure 23:
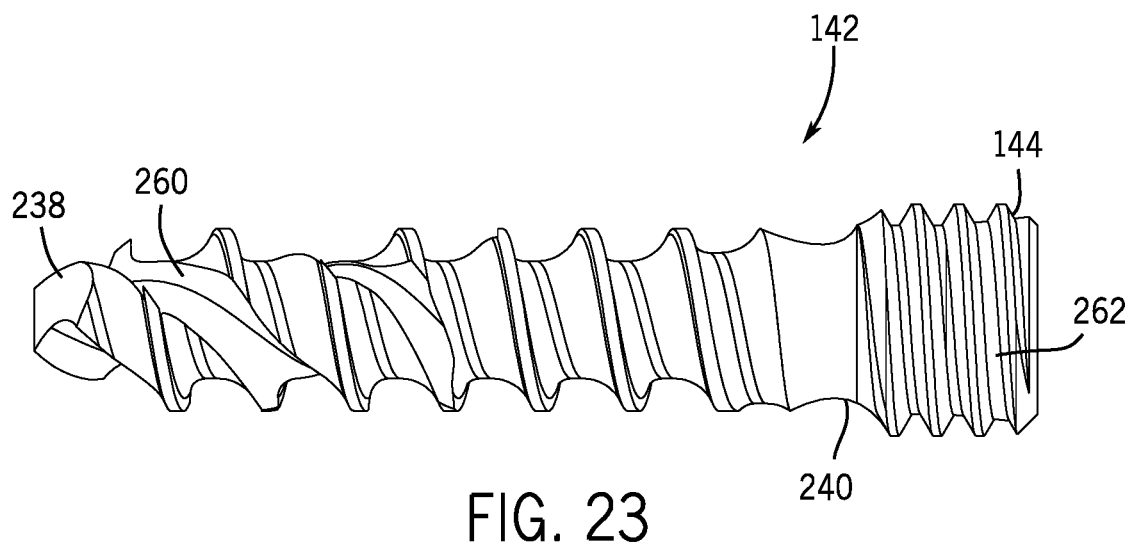
FIG. 23 is a side elevation view of a bone screw in accordance with an embodiment of the present disclosure.
Figure 24:
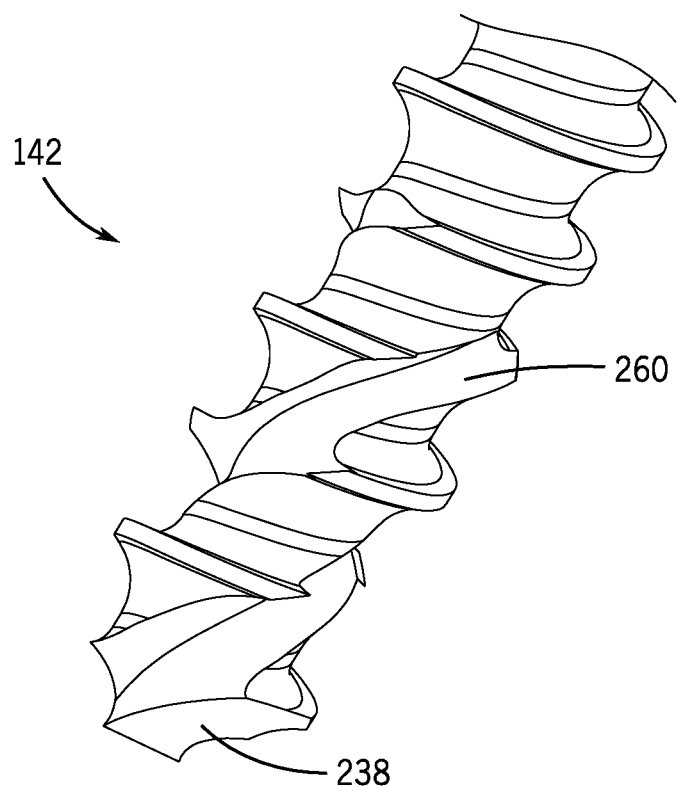
FIG. 24 is an enlarged, fragmentary view of the tip of the bone screw of FIG. 23 in accordance with an embodiment of the present disclosure.
Figure 25:
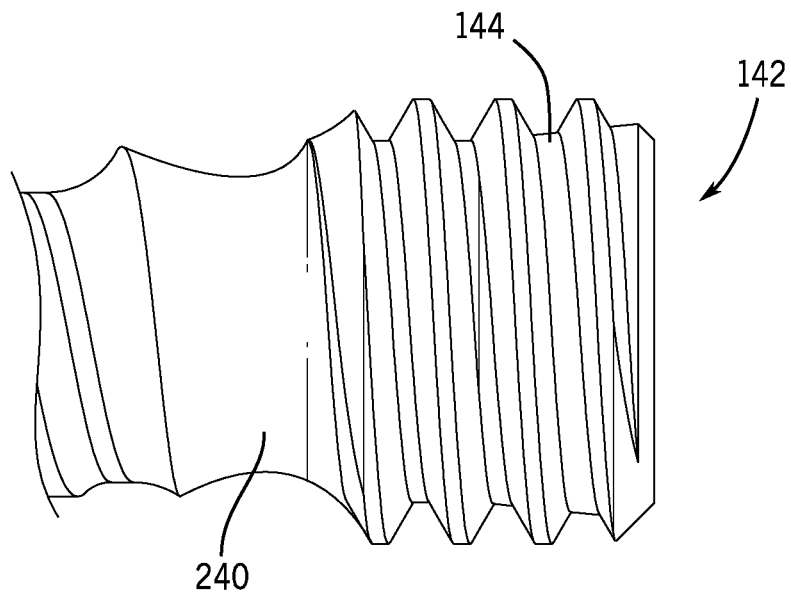
FIG. 25 is an enlarged, fragmentary view of the screw head of the bone screw of FIG. 23 in accordance with an embodiment of the present disclosure.

Referring now to FIGS. 20-22, in another embodiment, the delivery device 100 may include a positioning shaft 232 inserted within a lumen 234 of a cannulated drill or driver member 172. The positioning shaft 232 may include a distal tip feature 236 that is operable to preset the angle of the first end 174 of the drill or driver member 172 for proper bone screw insertion (see FIG. 22). For example, contact between the distal tip feature 236 of the positioning shaft 232 and the first end 174 of the drill or driver member 172 (e.g., the coupling 180) may cause the first end 174 to bend, flex, or articulate to a desired insertion angle. Once the proper insertion angle is preset in the drill or driver member 172, the drill or driver member 172 and the bone screw 142 are advanced adjacent the anchor shaft 102 and towards the fixation member 108 (see FIGS. 20 and 21 in sequence). Once the bone screw 142 has entered the fixation member 108, the positioning shaft 232 may be removed and the bone screw 142 may be torqued into place (see FIG. 22).

Turning now to FIGS. 33-46, in some embodiments, similar to the delivery device 100, the delivery device 300 includes a shaft 302 having proximal and distal ends or portions, 306, 304, and defining a lumen therein. The lumen may be a central lumen. As shown in FIGS. 33-37A, among others, the shaft 302 is an elongated anchor shaft 302 and may be generally long enough to extend from the distal portion 304 to a location outside a patient, where at least a portion of the anchor shaft 302 (e.g., the proximal portion 306) can be held and manipulated by a surgeon. The distal portion 304 and the proximal portion 306 may be two pieces attached together or, in some embodiments, may be formed monolithically or integrally together as a single piece. The anchor shaft 302, is a cannulated tube (see FIG. 36), and may be sized and shaped to releasably anchor the anchor shaft 302 to a fixation member 308 (e.g., a CAVUX™ Cervical Cage-L from Providence Medical Technology, Inc.) via a rod 600 and a screw guide 400. For example, the distal portion 304 of the anchor shaft 302 may be keyed or may include threading or the like to retain the anchor shaft 302 releasably to the screw guide 400 via the rod 600. In some embodiments, the screw guide 400 may be connected to the anchor shaft 302 so the delivery device 300 may be positioned irrespective to a position of a patient or the screw guide 400.

As illustrated in FIGS. 33-37A, among others, a screw guide 400 is coupled to the distal end 304 of the shaft and a handle 500 is coupled to the proximal end 306 of the shaft 302. The screw guide is positioned within the target area of the vertebrae to provide the correct (or predetermined) trajectory for screw deployment. In some embodiments, the screw guide 400 is operably connected to the anchor shaft 302 to direct the bone screw 600 for insertion in the fixation member 308. In one embodiment, the screw guide 400 abuts or is received by the anchor shaft 302 at the distal portion 304 of the anchor shaft 302 and adjacent the fixation member 308. As shown in FIGS. 37E-37G, the screw guide 400 may include a first or central lumen 469 for receipt of the rod and engagement with the shaft and one or more angled lumen 470 to define a trajectory for bone screw insertion. In some embodiments, the first or central lumen 469 includes grooves or threading 468 to engage the distal end of the shaft. In various embodiments, the angled lumen 470 of the screw guide 400 may be formed as part of the screw guide or may be removable. For example, when the screw guide 400 is positioned adjacent the fixation member 308 (i.e., "docked" or secured by the rod 600), the angled lumen 470 may be concentric with at least one securement or bone screw aperture 360 of the fixation member 308. Once docked against the fixation member 308, the angled lumen 470 of the screw guide 400 directs the bone screw 142 into proper alignment with the fixation member 308. In some embodiments, the angled lumen 470 may be offset from the rod receiving portion 480 of the screw guide 400.

Figure 33:
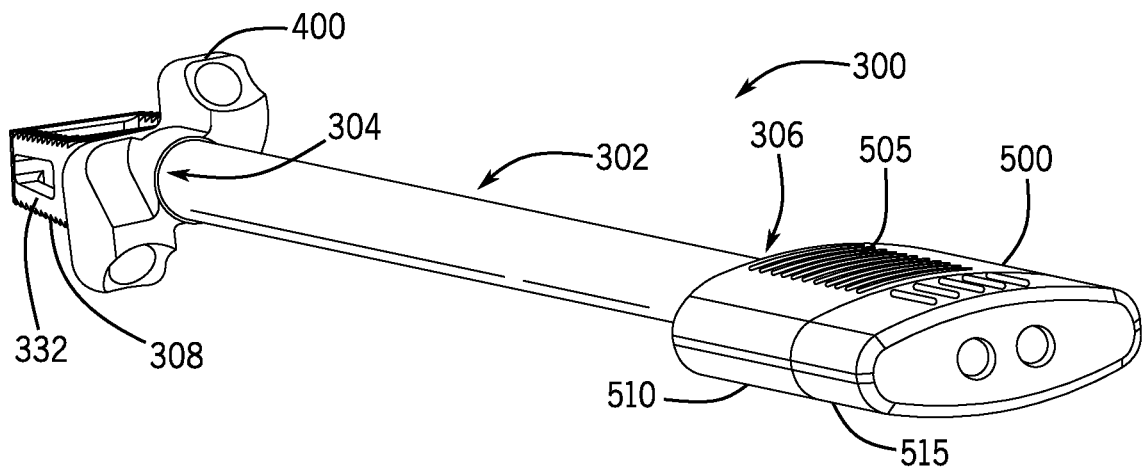
FIG. 33 is a perspective view of a delivery device and fixation member in accordance with an embodiment of the present disclosure.
Figure 34:
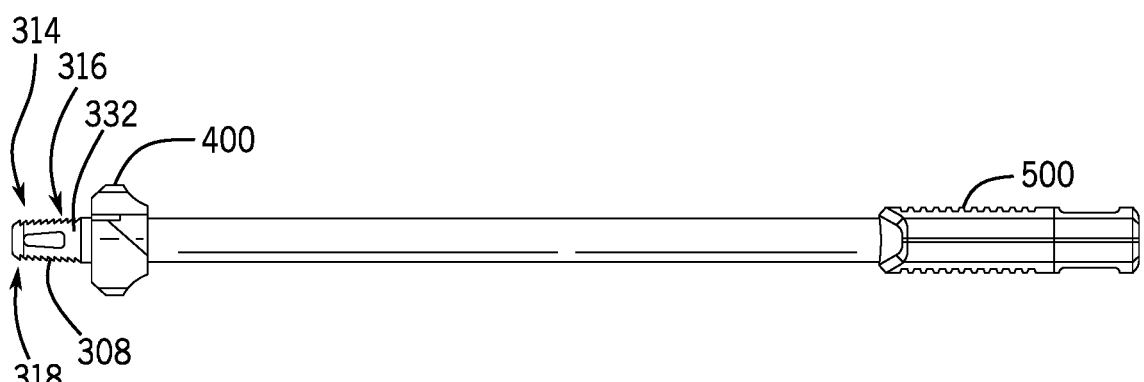
FIG. 34 is a side elevation view of the delivery device and fixation member of FIG. 33.
Figure 35:
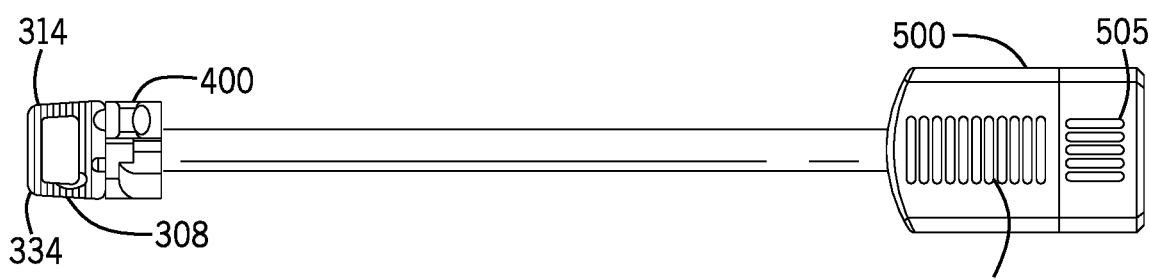
FIG. 35 is a top view of the delivery device and fixation member of FIG. 33.

The handle 500 is configured to release the cage or fixation member 308 attached or coupled to the screw guide 400 at the distal end of the device 300 (see FIGS. 33-35). The handle 500 is generally elliptical in shape and includes grip features 505 to help the user grasp and manipulate the handle. The grip features 505 may be elongate grip features positioned either horizontally or vertically on the handle. The grip features 505 may be made of rubber or other suitable polymer. The handle 500 may include a first portion 510 and a second portion 515. The first portion 510 may be fixed or stationary relative to the shaft 302. The second portion 515 may rotate or turn relative to the first portion 510 to release the fixation member 308, as described in more detail below.

Figure 36:
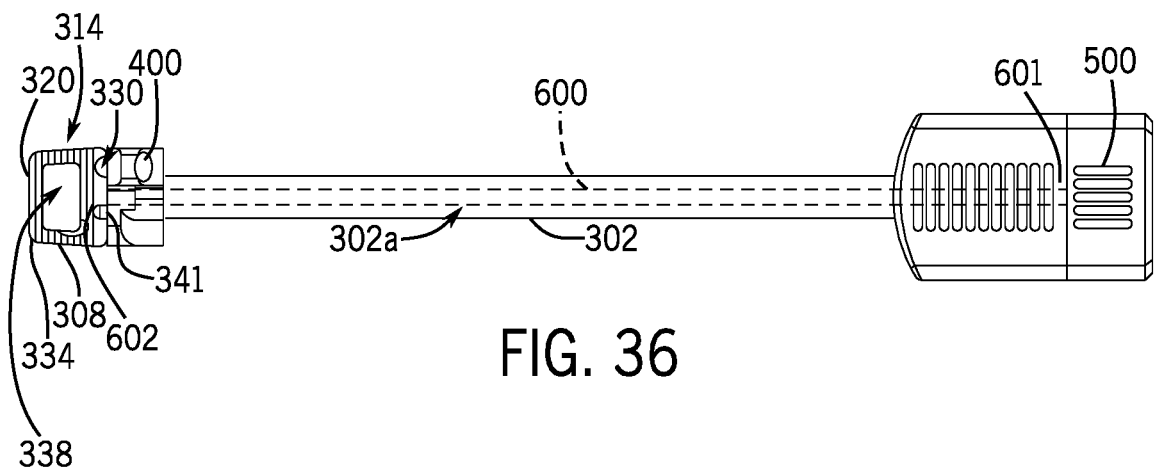
FIG. 36 is the top view of FIG. 35 showing an internal rod or elongate member that connects a handle to the fixation member.
Figure 37A:
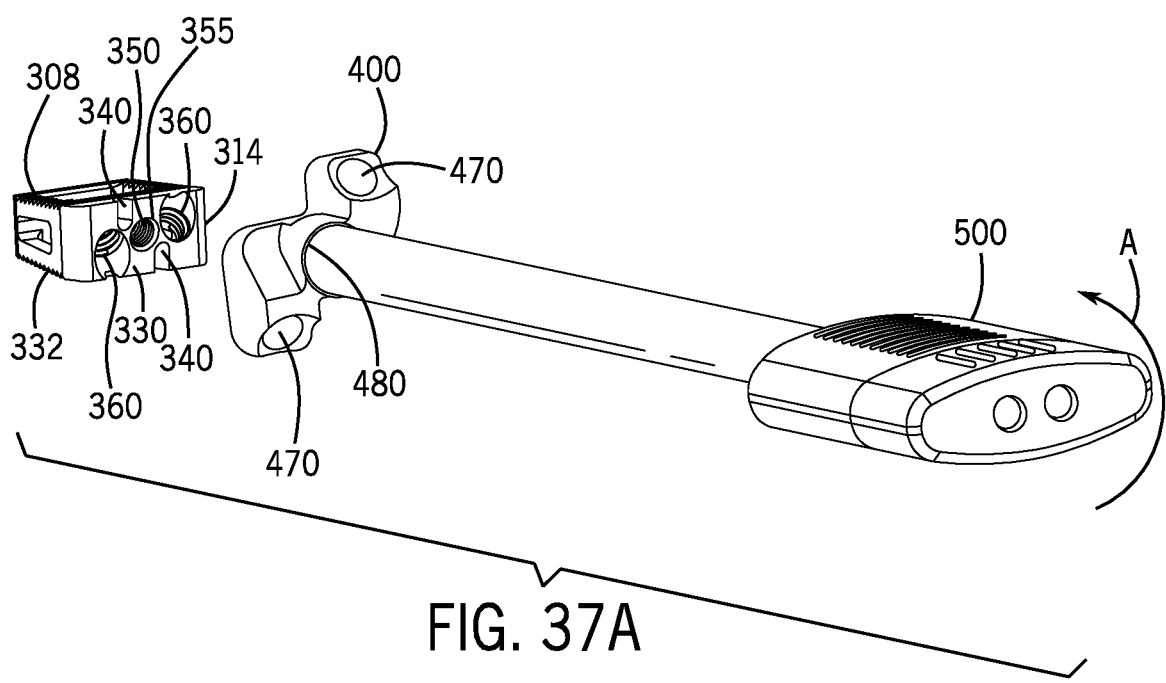
FIG. 37A is the perspective view of FIG. 33 showing the fixation member separated from the delivery device.
Figure 37B:
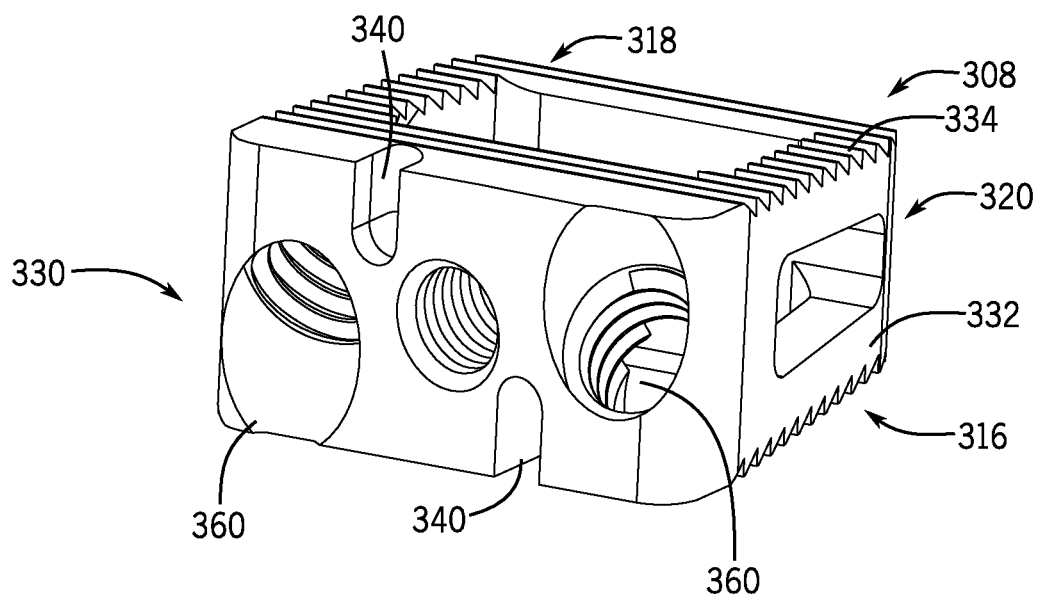
FIGS. 37B, 37C, 37D show a perspective, top and cross section view, respectively, of the fixation member of FIG. 37A.
Figure 37C:
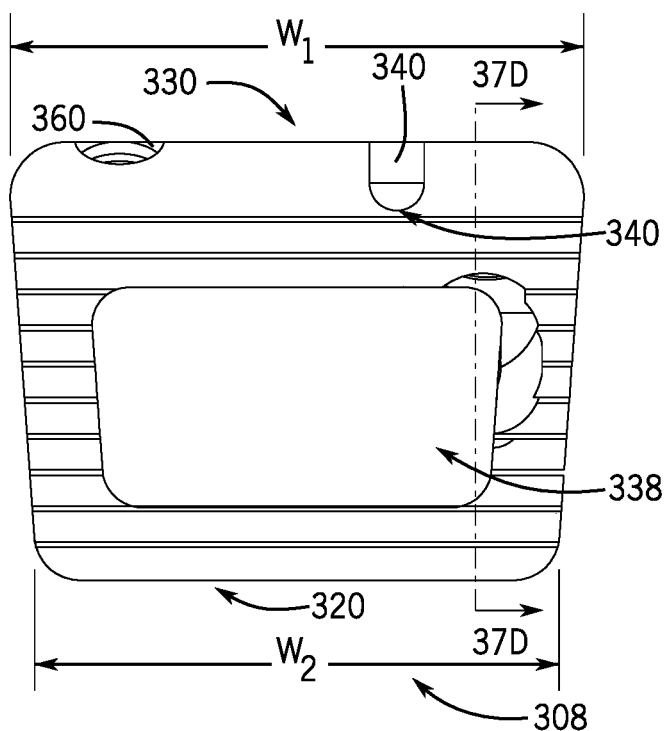
Figure 37D:
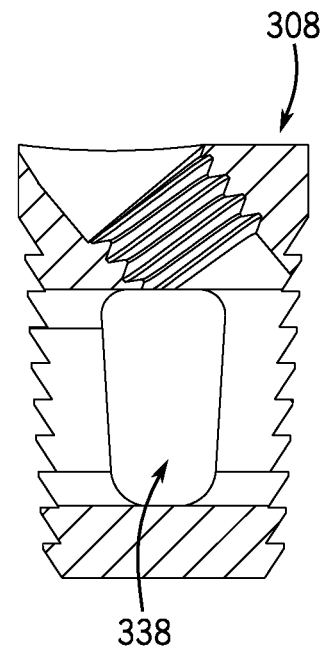
Figure 37E:
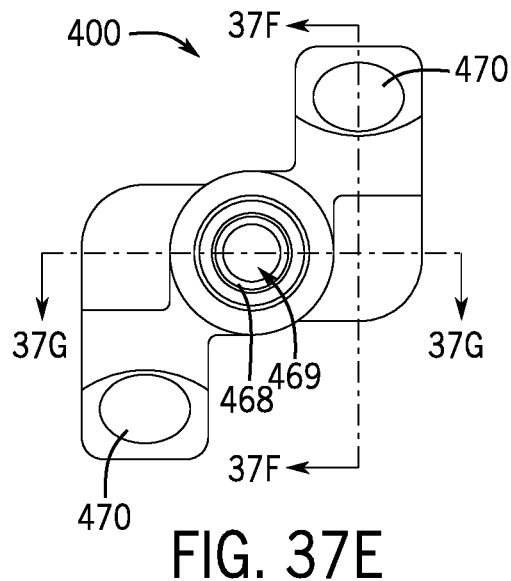
FIGS. 37E, 37F, 37G show an isometric view and two cross section views, respectively, of the screw guide.
Figure 37F:
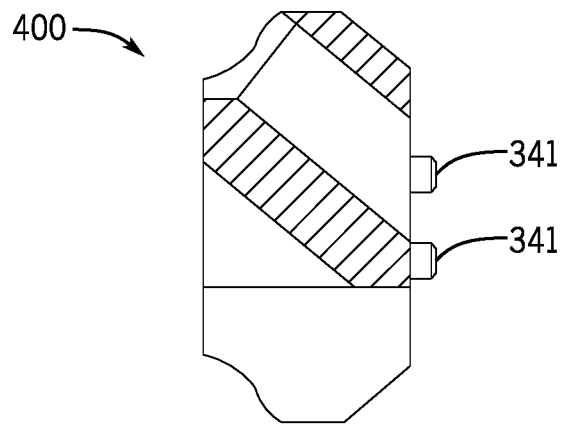
Figure 37G:
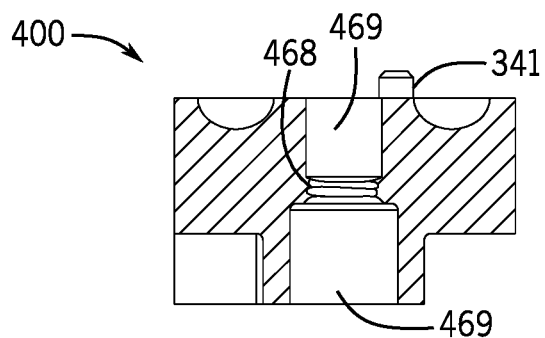

As depicted in FIG. 36, a rod or elongate member 600 may be positioned in the shaft lumen 302a and the rod includes both proximal 601 and distal 602 ends. The rod 600 may be solid or hollow and may be made of any appropriate material. The handle 500, which may be a cage release handle, is coupled to a proximal end 601 of the rod 600 and the fixation member 308 is coupled to the distal end 602 of the rod 600. The distal end 602 of the rod 600 may be threaded (not shown) for engagement with the threading 350 in the rod receiving aperture 355 in the fixation member 308. As can be understood from FIG. 37, the handle may be rotated in the direction of arrow A to unthread or release the fixation member 308 from the rod.

As indicated throughout, the fixation member may be releasably coupled with the delivery device. The fixation member 308 may be sized and shaped to fit snugly (e.g., a friction fit) into or otherwise engage or abut adjacent vertebrae in a disc joint space between two adjacent vertebrae (see e.g., FIG. 2, which illustrates a different embodiment but it is understood that the fixation member 308 fits in a similar location to that shown). As described herein, the fixation member 308 is operable to fixedly engage two adjacent vertebrae of a cervical spine (see e.g., FIG. 2) to fuse the two adjacent vertebrae together (e.g., C5 and C6 shown in FIG. 2). As perhaps best seen in FIGS. 34-37G, the fixation member 308 includes a main body 314 defined by opposing top and bottom surfaces 316, 318, opposing front and rear surfaces 320, 330, and opposing side surfaces 332. Bone screw receiving apertures 360 are defined in at least the rear surface 330. In one embodiment, there are two bone screw receiving apertures 360 configured to receive bones screws or other fasteners 700 for securing the fixation member 308 to the respective vertebral surface. The apertures 360 are angled to provide a specific trajectory for the bone screw 600 as described in more detail below.

The fixation member 308 may be generally cuboid in shape and may include engagement features 334 to retain the fixation member 308 fixedly within the disc joint space. For example, the top and bottom surfaces 316, 318 may include a plurality of directional projections 334 that allow the fixation member 308 to be inserted into a disc space but also limit its removal. For instance, the projections 334 may be shaped to resemble a sawtooth waveform in cross-section (see FIG. 33, 37B, 37D, 42), with vertical sections 336 of the projections 334 facing towards the front surface 320. As shown in FIGS. 36, 37A-D, 42, and others, the projections 334 may be horizontally spaced (e.g., in uniform rows) and may extend substantially between the opposing side surfaces 332 of the main body 314. To reduce weight and offer cross sectional areas for bone bridging (e.g., packing of bone graft material to promote bone growth after implantation), the fixation member 308 may include a plurality of cavities 338 defined in the surfaces of the fixation member 308 (e.g., the opposing top and bottom surfaces 316, 318 and the opposing side surfaces 332, see e.g., FIGS. 37B, 37C). In some embodiments, the cavities 338 may interconnect such that the main body 314 may be considered hollow. The fixation member may be tapered. That is, the width, $W_1$, of a rear surface 330 may be greater than the width, $W_2$, of the front surface 320 (see, e.g., FIG. 37C). The fixation member may be made of bone or bone substitute material or a biocompatible metal, ceramic, polymer, or some combination thereof. Examples include metals such as titanium, stainless steel, cobalt chrome, chro-moly and polymers such as Polycarbonate, PEI, UHMW PE, ABS, PEEK etc.

In some embodiments, and as shown in FIGS. 37A-D, the fixation member 308 further includes screw guide engagement features 340. The engagement features 340 may be slots, U-shaped apertures or other feature configured to receive a corresponding engagement feature 341 on the screw guide 400. When engaged, the features 340, 341 serve to secure the fixation member 308 and screw guide 400 for delivery. Engagement feature 341 may be shaped as a pin, u-shaped protrusion, or other configurations that match the corresponding shape of feature 340 (see FIGS. 37E, 37F and 37G). The paired, diagonally opposed positions of the two engagement features 341 provide a means to eliminate rotational movement of the fixation member 308 relative to the screw guide 400.

Figure 38:
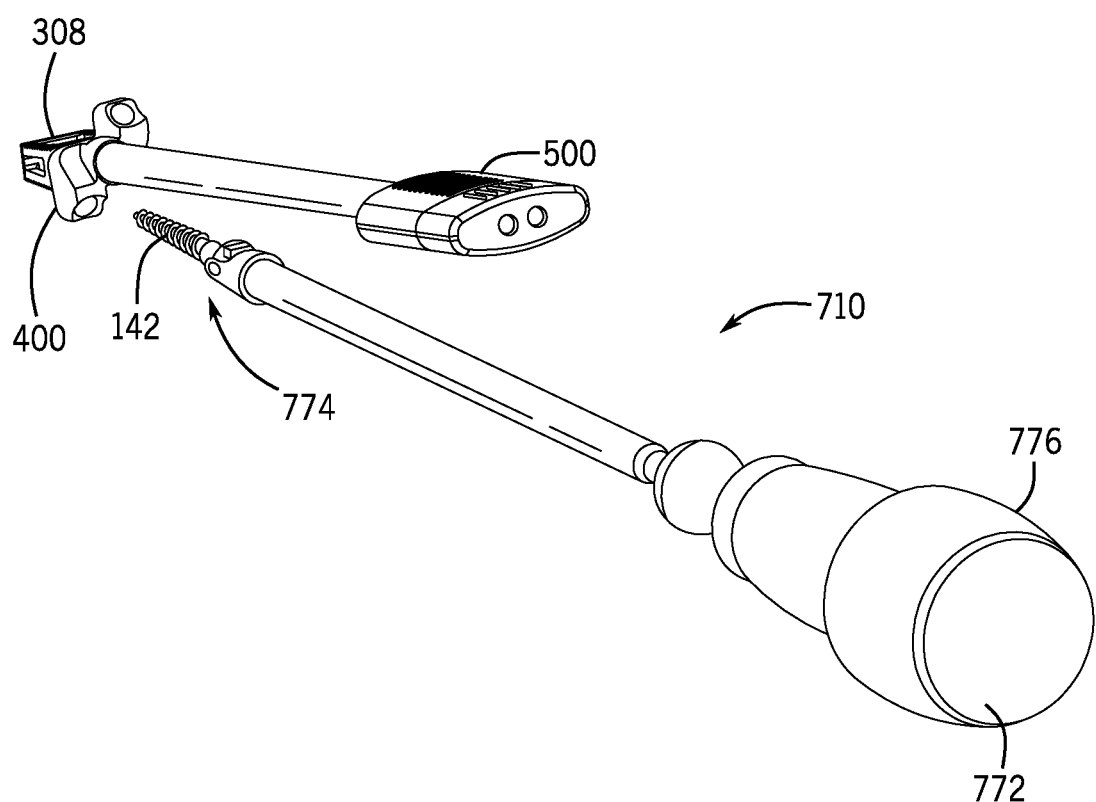
FIG. 38 is the perspective view of FIG. 33 wherein a bone screw and driver member are also illustrated.
Figure 39:
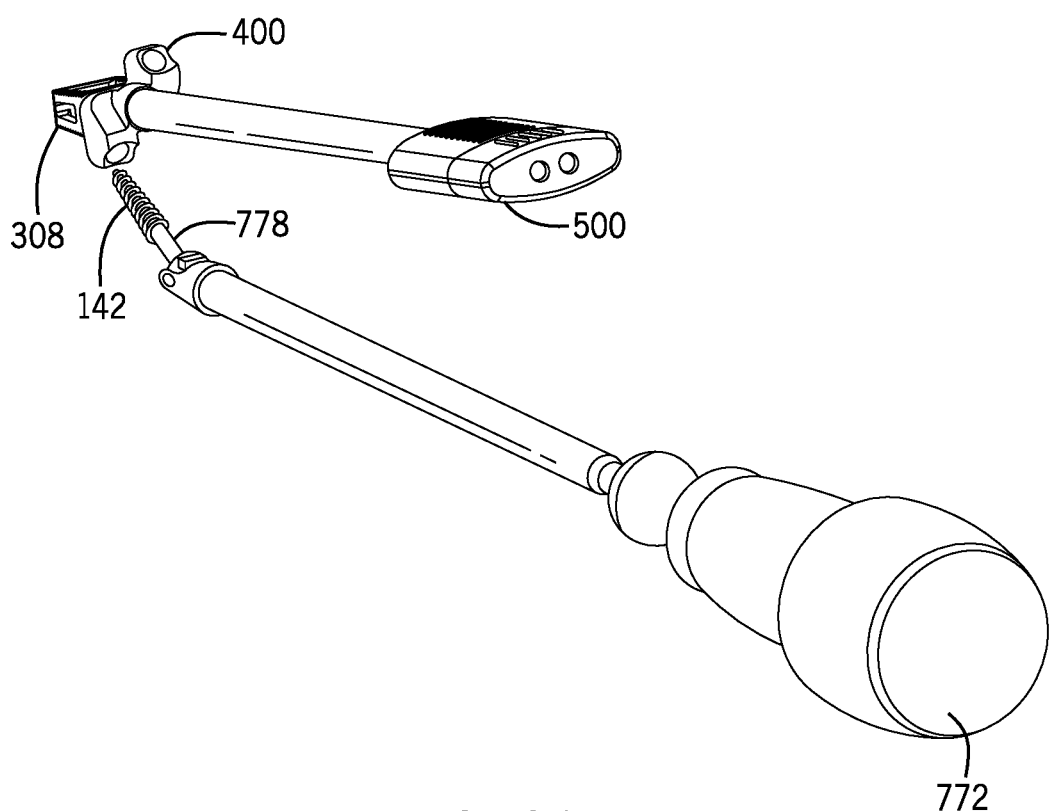
FIG. 39 depicts the bone screw shown in FIG. 38 entering a screw guide of the delivery device.
Figure 40:
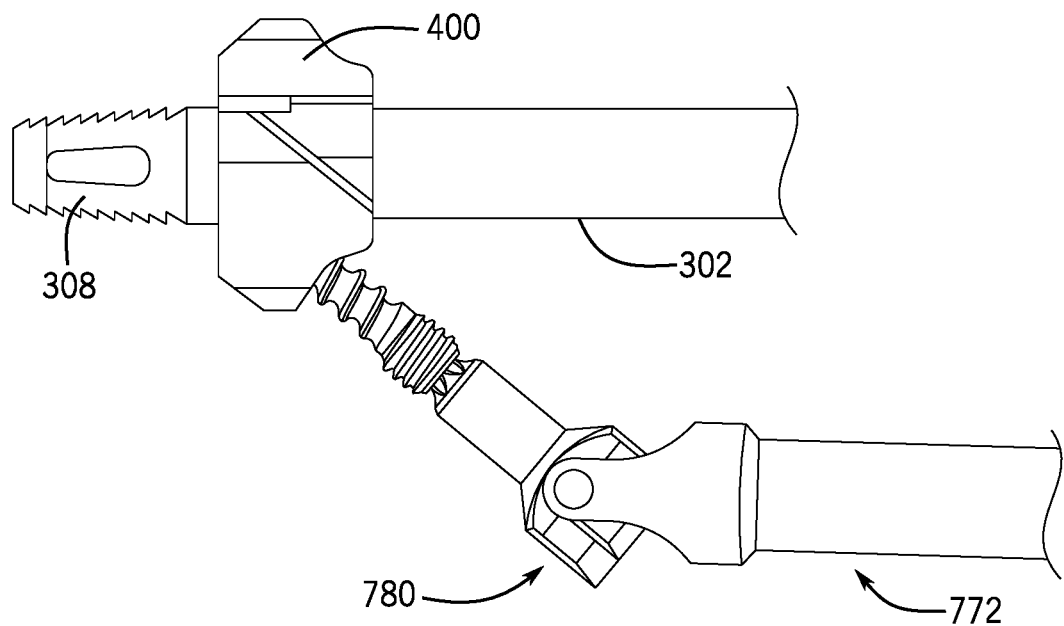
FIG. 40 is a side view of FIG. 39.
Figure 41:
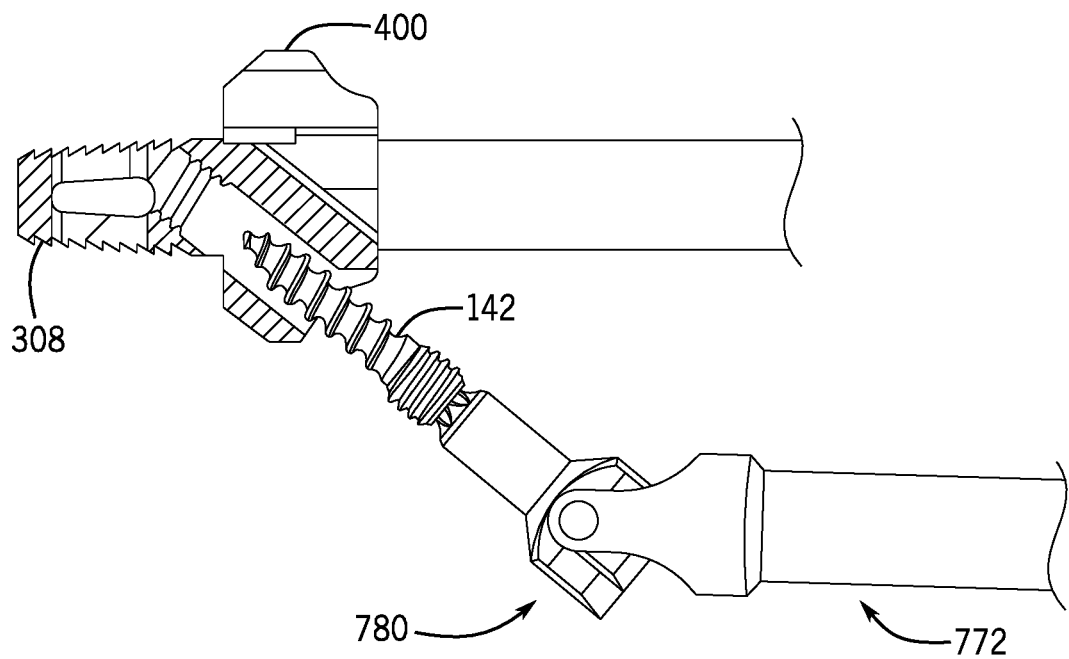
FIG. 41 is a cross section view of FIG. 40 about line 1-1.

As shown in FIG. 38, the system may further include a bone screw 142 coupled to a driver 772. The screw may be coupled via a close friction fit or light press fit. The screw is accepted by or received in the fixation member, as shown in FIGS. 39-41, among others. As also shown in these figures, the coaxial instruments (e.g. the screw guide and the driver) are either angled or articulating, or both, to provide angled screw deployment with minimal tissue retraction.

As illustrated in FIG. 38-45, in an exemplary embodiment, the screw delivery system 710 may include a drill or driver member 772 to both advance the bone screw 142 towards the fixation member 308 and drive the bone screw 142 into the fixation member 308 and into an adjacent vertebra. The drill or driver member 772 may be an elongated shaft and may include a first end 774 and a second end 776 extending from the first end 774. The drill or driver member 772 is a solid shaft and may be generally long enough to extend from the first end 774 to a location outside a patient, where at least a portion of the drill or driver member 772 (e.g., the second end 776) can be held and manipulated by a surgeon. In other embodiments, the shaft may be a cannulated tube. Once the bone screw 142 is driven within one of the securement apertures 360 of the fixation member 308 by the drill or driver member 772, the drill or driver member 772 may be removed from the screw guide lumen 470, then re-engaged with the second screw guide lumen 470 to repeat the process for subsequent bone screw insertion in other securement apertures 360, if any, of the fixation member 308.

With continued reference to FIGS. 38-45, for instance, the drill or driver member 772 may be operable to releasably grip the bone screw 142 until the bone screw 142 is driven into position within a disc joint space. For example, the first end 774, which may include a bit 778 for corresponding driving engagement with the screw head 144 of the bone screw 142 (see FIG. 42), may releasably retain the bone screw 142 through friction fit, interference fit, temporary attachment means, or other temporary securement mechanisms. In some embodiments, the first end 774 may flex, bend, or articulate in relation to the second end 776 to allow proper alignment of the bone screw 142 within the screw guide 400 and the fixation member 308. For instance, the first end 774 may include a coupling 780 that permits the drill or driver member 772 to rotate and articulate with the bone screw 142 at a specified angle. In some embodiments, the specified angle is between 30 and 70 degrees from collinear to the anchor shaft 302. As one example, the coupling 780 may take the form of a universal joint 790 that permits offset rotation of the first end 774 in relation to the second end 776 of the drill or driver member 772 (see FIG. 44). That is, the joint is a universal articulating joint. In other examples (see above), the coupling 780 may be a resiliently deformable coil spring that is capable of transmitting torque to the bone screw 142 at a desired angular trajectory. As yet another example, the coupling 780 may be a laser cut tube portion that resiliently deforms to a desired angular trajectory. Although three examples are provided, the coupling 780 may include other deformable mechanisms, including without limitation any combination of the three examples discussed above.

Figure 42:
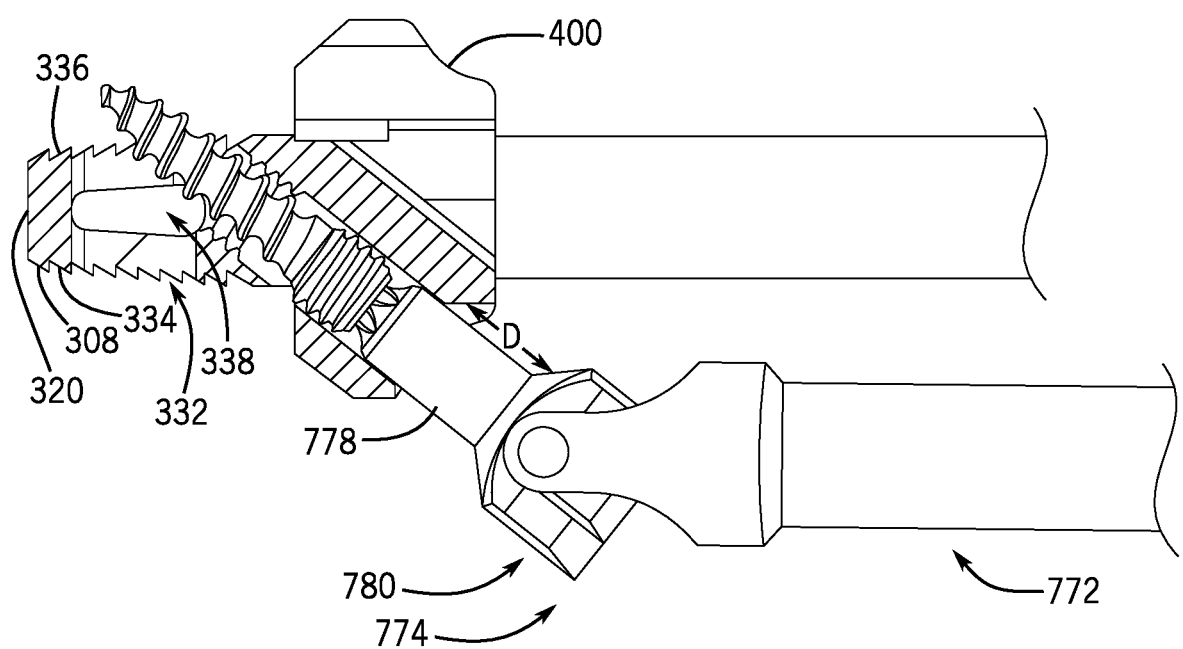
FIG. 42 is an enlarged view of FIG. 41 wherein the bone screw has advanced to the fixation member.
Figure 43:
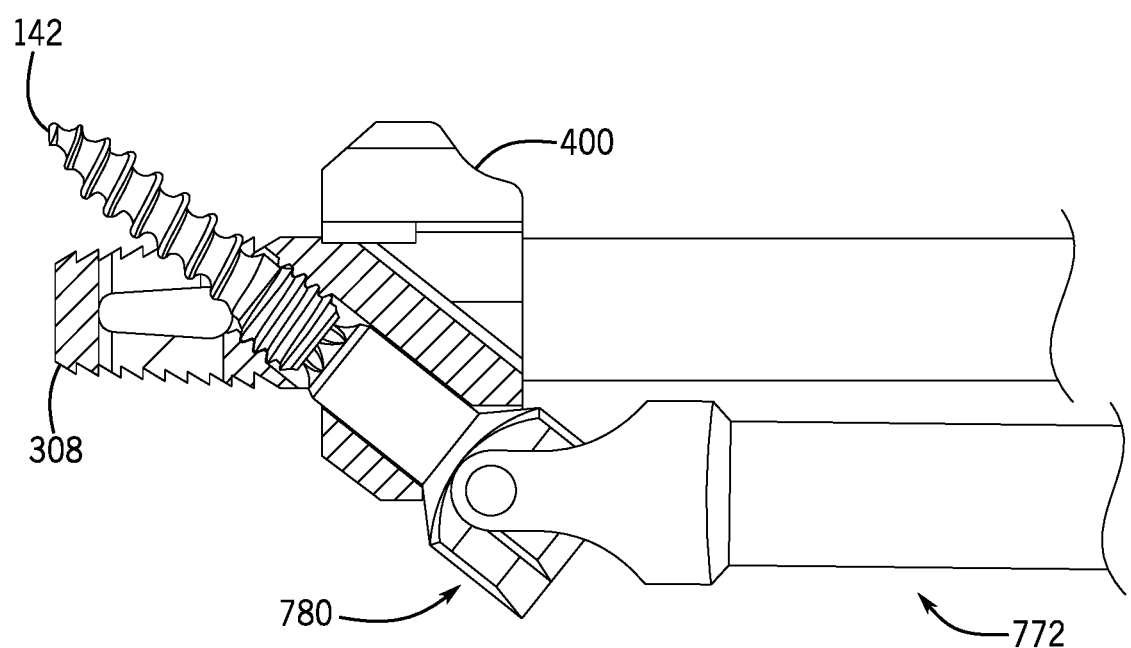
FIG. 43 is the view of FIG. 42 wherein the bone screw has advanced further into the fixation member.
Figure 46:
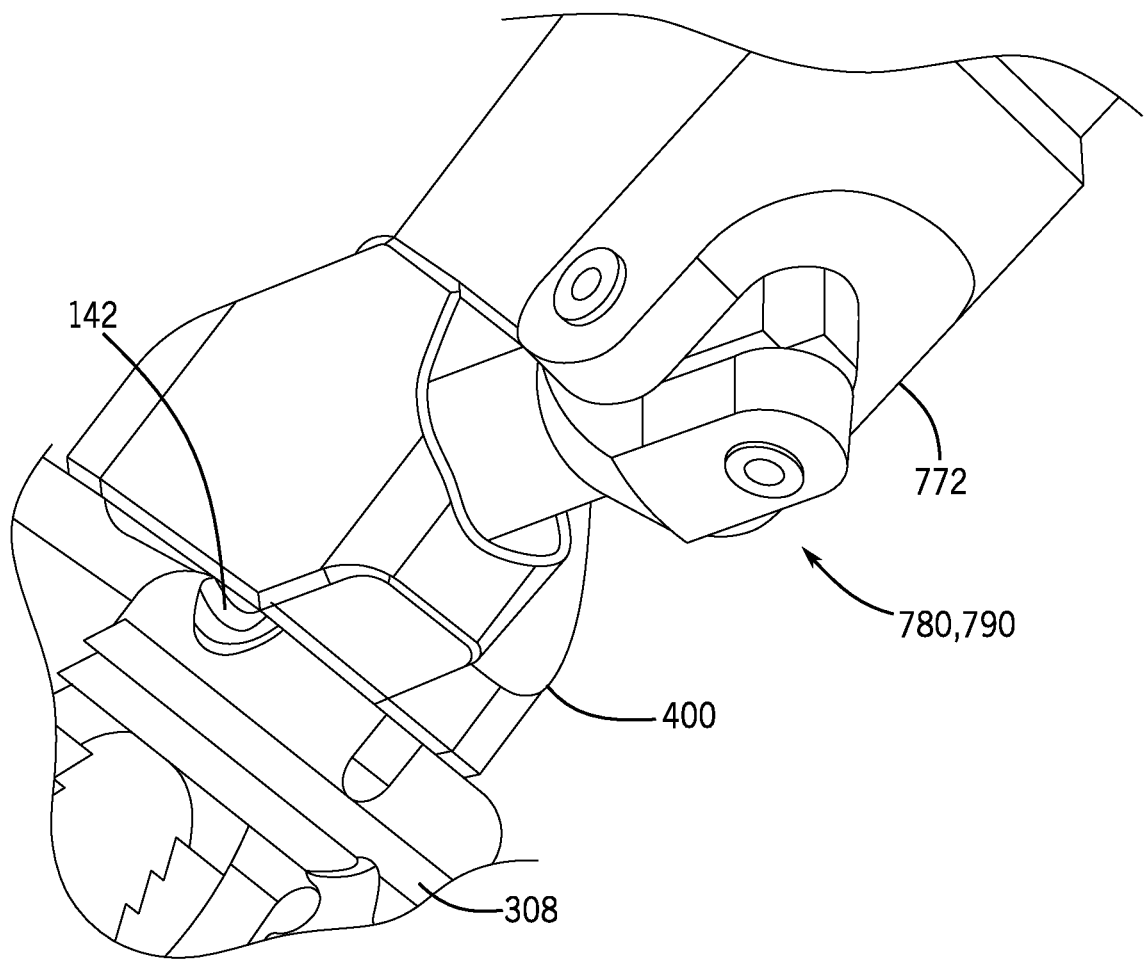
FIG. 46 is an enlarged view of the driver and screw guide of FIG. 45.

As illustrated in FIG. 42, in use, the screw 142 is coupled or is coupled directly to the driver 772, which guides the screw 142 through the screw guide lumen 470 and into the fixation member 308. The screw 142 is attached securely to the driver bit by a friction fit. The dual-sided arrow shows the distance D between the shoulder of the driver bit 778 and the screw guide 400. In one embodiment, the driver 772 and screw 142 are rotated clockwise as they are advanced. FIG. 43 depicts the decreased distance between the shoulder of the driver bit 778 and the screw guide 400. More specifically, Position 1 points to the contact between the shoulder of the driver bit 778 and the screw guide 400. While the driver bit 778 can be rotated in place, it can no longer advance. FIG. 46 illustrates an enlarged view of the contact or engagement surfaces that will prevent further advancement of the driver while allowing the driver to rotate in place. The surfaces are matching concave and convex surfaces.

Turning back to FIG. 43, Position 2 of FIG. 43 shows the threaded head of the screw 142 engaging with the threaded lumen of the fixation member 308. As the driver 772 is rotated, the screw 142 is advanced by engagement with the thread features 360. The screw 142 includes one or more locking or anti-backout features, such as a self-locking thread and/or an interference thread at the screw head, to help anchor the screw 142 in the fixation member.

Figure 44:
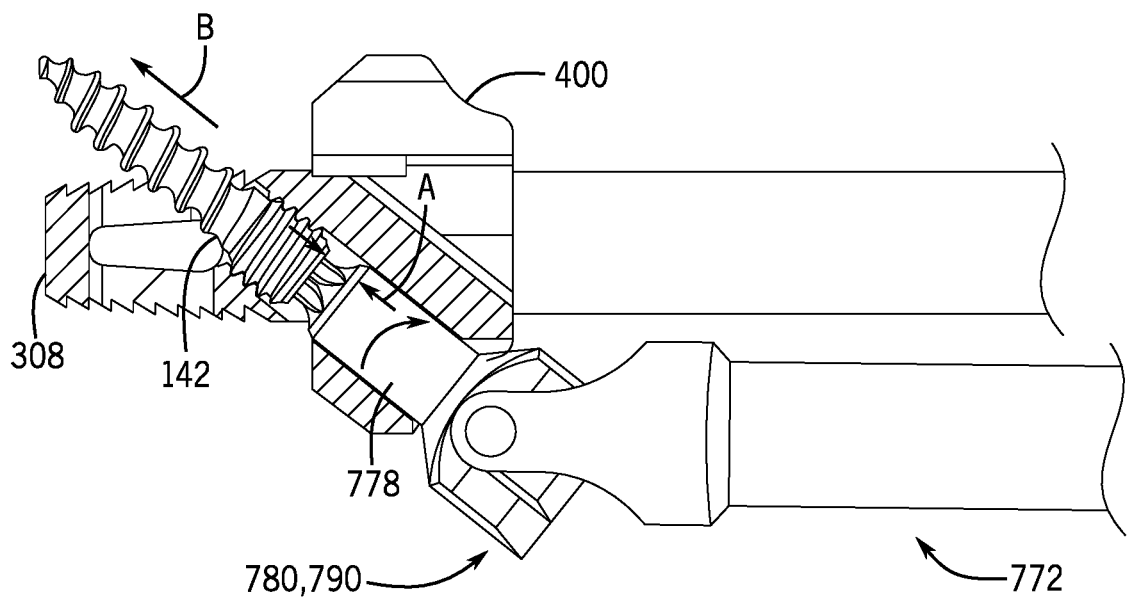
FIGS. 44 and 45 illustrate deployment of the bone screw shown in FIG. 43.
Figure 45:
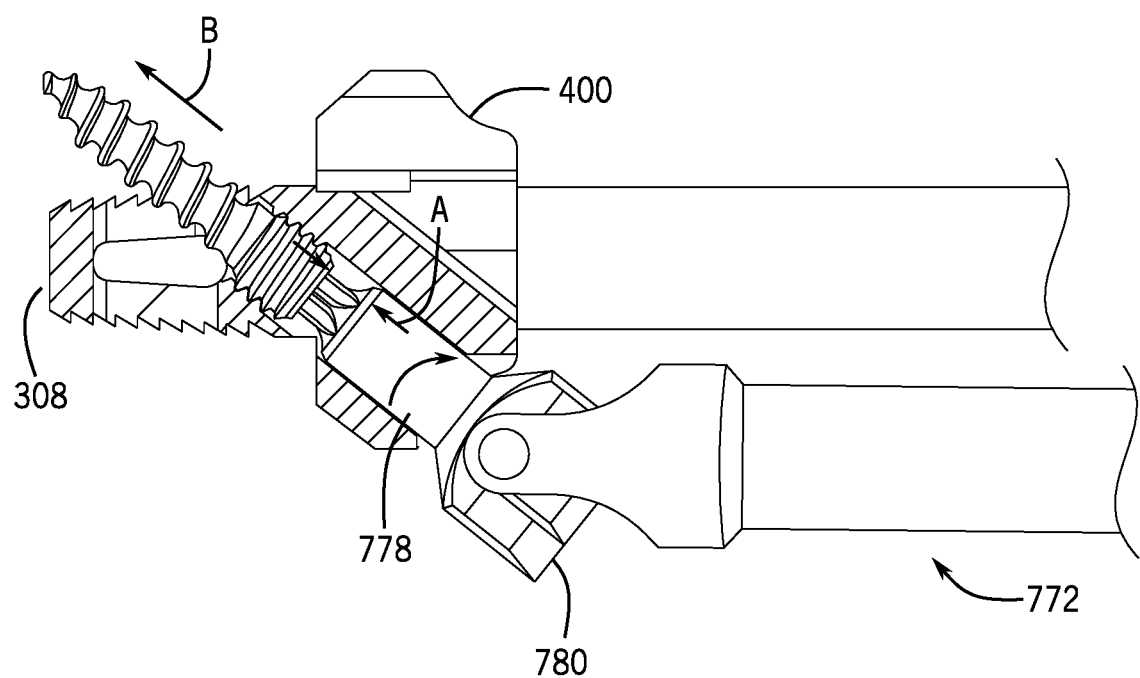

As can be understood from FIG. 44, as the screw 142 is advanced in the direction of arrow B through the screw guide 400 (and the driver 772 rotates in place), the screw 142 begins to disengage from the driver bit 778, as shown by the dual sided arrow A. That is, the friction fit (light press fit) between the screw head and driver bit is broken. FIGS. 45 and 46 illustrate the system 710 as screw deployment is completed. As shown, the screw 142 has moved off from the driver bit 778 (shown by arrow A) enough to break the friction fit completely, yet there is enough engagement between the driver bit and the screw head to complete the screw rotation and deploy it fully. The driver 772 can now be removed from the screw guide 400, leaving the screw locked or secured in place within the fixation member 308.

Figure 26:
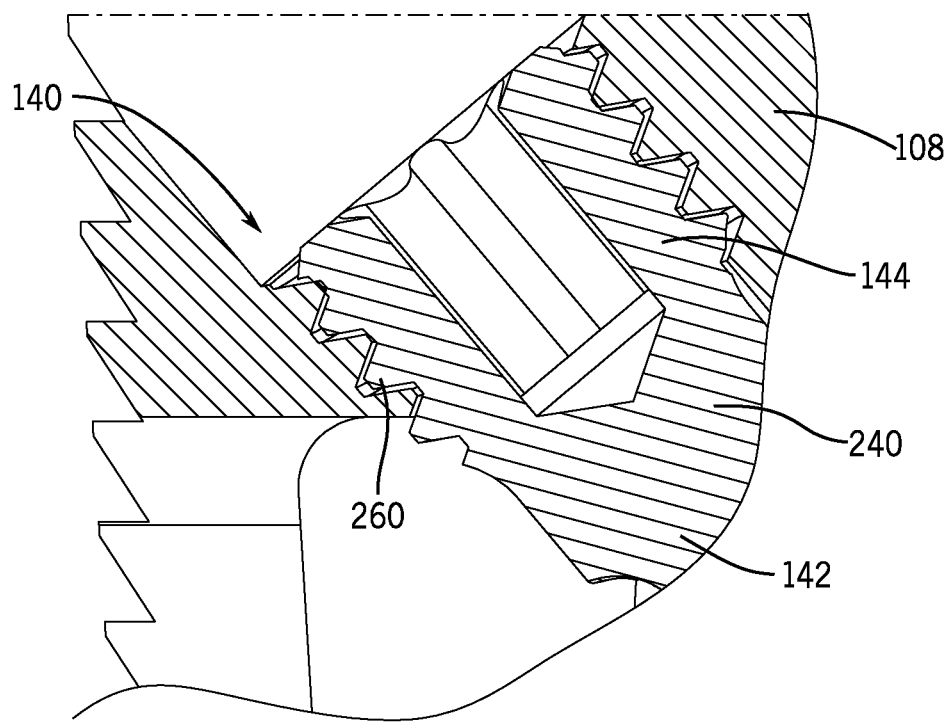
FIG. 26 is a fragmentary cross-sectional view of the bone screw of FIG. 23 in accordance with an embodiment of the present disclosure.

Referring back to FIGS. 23-26, and as shown in FIGS. 38-46, the bone screw 142 in each of the embodiments described above and below may be self-drilling, self-tapping, and locking. In embodiments, the screw is a solid screw (i.e., it is not hollow and/or does not include a lumen defined within the screw body). As illustrated, the bone screw 142 may include a distal tip 238 and a proximal end 240 including the screw head 144. In some embodiments, the bone screw 142 may include a helical cutting flute 260 fading out from the distal tip 238 towards the proximal end 240. The distal tip 238 may include a sharp tip angle to encourage bone and/or tissue cutting. In some embodiments, an outer portion 262 of the screw head 144 may be threaded to engage corresponding threads of the securement apertures 140 (see FIG. 26). As shown in FIG. 26 and FIG. 45, among others, to lock the bone screw 142 to the fixation member 108, 308 the minor diameter of the thread feature on the outer portion 262 of the screw head 144 may outwardly taper to create an interference fit with the threaded securement apertures 140 of the fixation member 108, 308 effectively locking the bone screw 142 in place and limiting back out. In some embodiments, the thread pitch on the outer portion 262 of the screw head 144 at the last thread may also be greater than or less than the thread pitch on the fixation member 108, 308, thereby creating an interference fit on the last turn(s) when driving the screw 142 into the fixation member 108, 308.

The delivery device 100, 300, drill or driver member 172, 772 and fixation member 108, 308 may be formed from a variety of materials and means. For example, the delivery device 100, 300, including the anchor shaft 102, 302 guide member 150, screw guide 168, and guidewires 196, 222, may be formed from stainless steel, titanium alloy, cobalt chromium alloy, ceramics, plastics (e.g., polyethylene), or other material suitable for use in sterile surgical environments. The drill or driver member 172, 772 and fixation member 108, 308 may be similarly configured. In some embodiments, the delivery device 100, 300 and the drill or driver member 172, 772 may include hydrophilic and/or hydrophobic coatings for lubrication needs. The devices, systems and apparatus may be single use and/or disposable or include single use and/or disposable components.

All relative and directional references (including: upper, lower, upward, downward, left, right, leftward, rightward, top, bottom, side, above, below, front, middle, back, vertical, horizontal, and so forth) are given by way of example to aid the reader's understanding of the particular embodiments described herein. They should not be read to be requirements or limitations, particularly as to the position, orientation, or use unless specifically set forth in the claims. Connection references (e.g., attached, coupled, connected, joined, and the like) are to be construed broadly and may include intermediate members between a connection of elements and relative movement between elements. As such, connection references do not necessarily infer that two elements are directly connected and in fixed relation to each other unless specifically set forth in the claims.

Those skilled in the art will appreciate that the presently disclosed embodiments teach by way of example and not by limitation. Therefore, the matter contained in the above description or shown in the accompanying drawings should be interpreted as illustrative and not in a limiting sense. Thus, it is intended that the scope of the present disclosure should not be limited by the particular embodiments described above.

What is claimed is:

1. An apparatus for guiding a fixation member to a cervical disc joint space in a spine in an ACDF procedure, the apparatus comprising:
   a delivery device comprising:
      an anchor shaft comprising a central lumen defining a longitudinal axis, a distal portion and a proximal portion extending from the distal portion;
      a guide member operably associated with the anchor shaft, the guide member defining a first lumen coaxial with the central lumen, two angled lumen offset from the first lumen and at least one fixation member engagement feature; and
   a fixation member comprising a main body having top and bottom surfaces, each with a cavity defined in the respective surface, at least one threaded opening and at least one guide member engagement feature such that when the guide member engagement feature receives the fixation member engagement feature, the engagement hinders rotation of the fixation member relative to the guide member,
   wherein the fixation member further comprises two angled threaded apertures defined in the main body and offset from the at least one threaded opening, one of the two angled threaded apertures extending toward the top or bottom surface to guide a fastener through the cavity defined in the respective surface.

2. The apparatus of claim 1, further comprising a rod member having at least one threaded end extending at least partially through the central lumen of the anchor shaft to releasably engage the threaded opening of the fixation member.

3. The apparatus of claim 2, further comprising a handle, the handle operably coupled to the proximal portion of the anchor shaft and rotatably coupled to the rod, wherein rotation of the rod releasably engages the rod with the fixation member.

4. The apparatus of claim 1, wherein the at least one fixation member engagement feature includes at least one slot.

5. The apparatus of claim 1, wherein the two angled lumen comprise a first angled lumen defining a first trajectory that is angled relative to the longitudinal axis and a second angled lumen defining a second trajectory that is angled relative to the longitudinal axis.

6. The apparatus of claim 5, wherein the first trajectory is different from the second trajectory.

7. The apparatus of claim 5, wherein the first trajectory guides a first fastener to a superior vertebral surface and the second trajectory guides a second fastener to an inferior vertebral surface.

8. The apparatus of claim 1, wherein the two angled threaded apertures are coextensive or coaxial with a respective angled lumen of the guide member when the guide member and the fixation member are engaged and the other of the two angled threaded apertures extending toward the other of the top or bottom surface to guide a second fastener through the cavity defined in the respective surface.

9. The apparatus of claim 1, wherein when the guide member and the fixation member are engaged, the opening of the fixation member is coextensive or coaxial with the central lumen of the anchor shaft.

10. The apparatus of claim 1, wherein a surface of the guide member and a surface of the fixation member abut each other.

11. The apparatus of claim 1, wherein the guide member is slidably coupled with the anchor shaft.

12. A system for guiding and securing a fixation member to a cervical disc joint space in a spine in an ACDF procedure, the system comprising:
   a fixation member delivery device comprising:
      an anchor shaft comprising a central lumen defining a longitudinal axis, a distal portion and a proximal portion extending from the distal portion; and
      a guide member operably associated with the anchor shaft, the guide member defining a first lumen coaxial with the central lumen, two angled lumen offset from the first lumen and at least one fixation member engagement feature; and
   a fixation member comprising a main body having top and bottom surfaces, each with a cavity defined in the respective surface, at least one threaded opening and at least one guide member engagement feature such that when the guide member engagement feature receives the fixation member engagement feature, the engagement hinders rotation of the fixation member relative to the guide member; and
   a drive member having a first end operably associated with the guide member adjacent the anchor shaft,
   wherein the fixation member further comprises two angled threaded apertures defined in the main body and offset from the at least one threaded opening, one of two angled threaded apertures extending toward the top or bottom surface to guide a fastener through the cavity defined in the respective surface.

13. The system of claim 12 wherein the fixation member delivery device further comprises a rod having at least one threaded end extending at least partially through the central lumen of the anchor shaft to releasably engage the threaded opening of the fixation member.

14. The system of claim 13 wherein the fixation member delivery device further comprises a handle, the handle operably coupled to the proximal portion of the anchor shaft and rotatably coupled to the rod, wherein rotation of the rod releasably engages the rod with the fixation member.

15. The system of claim 12, wherein the two angled threaded apertures are coextensive or coaxial with a respective angled lumen of the guide member when the guide member and the fixation member are engaged and the other of the two angled threaded apertures extending toward the other of the top or bottom surface to guide a second fastener through the cavity defined in the respective surface.

16. The system of claim 15, further comprising at least one fastener, the at least one fastener received in one of the two angled threaded apertures of the fixation member to secure the fixation member to a vertebral surface.

17. The system of claim 16, wherein the at least one fastener is an anti-backout screw or a self-locking screw, with an interference thread at the head of the screw.

18. The system of claim 12, wherein the first end of the drive member includes a coupling that permits the drive member to rotate and/or articulate with a fastener at a desired angle to deploy the fastener at a desired angle with minimal tissue retraction.

19. The system of claim 18, wherein the coupling is selected from a group consisting of a universal joint, a coil spring, or a relief cut tube portion.

20. A method of implanting a spinal fixation implant, the method comprising:
  advancing a delivery apparatus into a disc joint space between two adjacent vertebrae in an ACDF procedure, the delivery apparatus comprising:
    an anchor shaft comprising a central lumen defining a longitudinal axis, a distal portion and a proximal portion extending from the distal portion;
    a guide member operably associated with the anchor shaft, the guide member defining a first lumen coaxial with the central lumen, two angled lumen offset from the first lumen and at least one fixation member engagement feature; and
    a fixation member comprising:
      a main body having top and bottom surfaces, each with a cavity defined in a respective surface,
      at least one threaded opening;
      two angled threaded apertures defined in the main body and offset from the at least one threaded opening, one of the two angled threaded apertures extending toward the top or bottom surface to guide a fastener through the cavity defined in the respective surface; and
      at least one guide member engagement feature such that when the guide member engagement feature receives the fixation member engagement feature, the engagement hinders rotation of the fixation member relative to the guide member;
  advancing a drill/drive member adjacent the delivery apparatus, the drill/drive member having the fastener releasably attached to a first end of the drill/drive member; and
  advancing the fastener through the one of the two angled lumen of the guide member to attach the fixation member to at least one of the two adjacent vertebrae.

* * * * *